(12) United States Patent
Hurtado et al.

(10) Patent No.: US 11,980,534 B2
(45) Date of Patent: May 14, 2024

(54) THREE-DIMENSIONAL SCAFFOLDS, METHODS FOR FABRICATING THE SAME, AND METHODS OF TREATING A PERIPHERAL NERVE OR SPINAL CORD INJURY

(71) Applicants: The Johns Hopkins University, Baltimore, MD (US); Rensselaer Polytechnic Institute, Troy, NY (US)

(72) Inventors: Andres Hurtado, Baltimore, MD (US); Ryan James Gilbert, Houghton, MI (US); Han Bing Wang, Houghton, MI (US); Jared M. Cregg, Houghton, MI (US); Michael E. Mullins, Houghton, MI (US); Martin Oudega, Munhall, PA (US)

(73) Assignees: Rensselaer Polytechnic Institute, Troy, NY (US); Johns Hopkins University, Baltimore, MD (US)

( * ) Notice: Subject to any disclaimer, the term of this patent is extended or adjusted under 35 U.S.C. 154(b) by 1154 days.

(21) Appl. No.: 16/524,473

(22) Filed: Jul. 29, 2019

(65) Prior Publication Data

US 2019/0350688 A1    Nov. 21, 2019

Related U.S. Application Data

(62) Division of application No. 13/638,923, filed as application No. PCT/US2011/030965 on Apr. 1, 2011, now Pat. No. 10,413,391.

(Continued)

(51) Int. Cl.
*A61F 2/00*    (2006.01)
*A61L 27/18*    (2006.01)
(Continued)

(52) U.S. Cl.
CPC .............. *A61F 2/00* (2013.01); *A61F 2/0063* (2013.01); *A61L 27/18* (2013.01); *A61L 27/383* (2013.01);
(Continued)

(58) Field of Classification Search
CPC .... D01D 5/0007; D01D 5/003; D01D 5/0038; D01D 5/0046; D01D 5/0076; A61F 2/00; A61F 2/0063
See application file for complete search history.

(56) References Cited

U.S. PATENT DOCUMENTS 5,147,387 A * 9/1992 Jansen ................... A61B 17/30
                                                     623/1.21
6,099,518 A * 8/2000 Adams .................. A61F 2/0063
                                                      604/523

(Continued)

*Primary Examiner* — Cachet I Proctor
(74) *Attorney, Agent, or Firm* — Barclay Damon LLP; Anthony P. Gangemi

(57) ABSTRACT

One aspect of the invention provides a three-dimensional scaffold including at least one layer of highly-aligned fibers. The at least one layer of highly-aligned fibers is curved in a direction substantially perpendicular to a general direction of the fibers. Another aspect of the invention provides a method for fabricating a three-dimensional scaffold. The method includes: electro spinning a plurality of fibers to produce at least one layer of highly-aligned fibers and forming the at least one layer of highly-aligned fibers into a three-dimensional scaffold without disturbing the alignment of the highly-aligned polymer fibers. A further aspect of the invention provides methods for using a three-dimensional scaffold to treat nerve or spinal cord injury.

14 Claims, 35 Drawing Sheets

Related U.S. Application Data

(60) Provisional application No. 61/320,088, filed on Apr. 1, 2010.

(51) Int. Cl.
*A61L 27/38* (2006.01)
*A61L 27/54* (2006.01)
*D01D 5/00* (2006.01)
*D06M 16/00* (2006.01)
*A61F 2/04* (2013.01)

(52) U.S. Cl.
CPC ........... *A61L 27/3834* (2013.01); *A61L 27/54* (2013.01); *D01D 5/0076* (2013.01); *D06M 16/003* (2013.01); *A61F 2/04* (2013.01); *A61L 2300/254* (2013.01); *A61L 2300/414* (2013.01); *A61L 2300/416* (2013.01); *A61L 2430/32* (2013.01); *A61L 2430/38* (2013.01)

(56) References Cited

U.S. PATENT DOCUMENTS

| | | | |
|---|---|---|---|
| 2002/0111543 A1* | 8/2002 | Penner | A61B 5/0031 606/139 |
| 2008/0147199 A1* | 6/2008 | Yost | B29C 48/09 435/395 |
| 2008/0220042 A1* | 9/2008 | Hashi | A61L 27/54 514/6.9 |
| 2009/0018643 A1* | 1/2009 | Hashi | A61L 31/146 623/1.15 |
| 2010/0310623 A1* | 12/2010 | Laurencin | A61L 27/58 514/16.7 |
| 2013/0018454 A1* | 1/2013 | Lelkes | D01F 6/70 427/2.24 |

* cited by examiner

THREE-DIMENSIONAL SCAFFOLDS, METHODS FOR FABRICATING THE SAME, AND METHODS OF TREATING A PERIPHERAL NERVE OR SPINAL CORD INJURY

CROSS-REFERENCE TO RELATED APPLICATIONS

This application is a divisional application of U.S. application Ser. No. 13/638,923, filed Jan. 14, 2013 and claims priority to PCT/US2011/030965 filed on Apr. 1, 2011 which claims the benefit of U.S. Provisional Patent Application Serial No. 61/320,088, filed Apr. 1, 2010, the contents of which are incorporated herein by reference in their entirety.

STATEMENT OF RIGHTS TO INVENTIONS MADE UNDER FEDERALLY SPONSORED RESEARCH

This work was supported by grant no. NINDS R21NS62392 and NICHD R15HD61096 from the National Institutes of Health. The U.S. Government has certain rights in this invention.

BACKGROUND OF THE INVENTION

In the United States, it is estimated that 11,000 individuals sustain spinal cord injuries each year. One major factor that limits treatment of spinal cord injury is the failure of axons to regenerate spontaneously after central nervous system (CNS) injury. Regeneration failure can be partially attributed to a limited intrinsic axon growth capacity of adult neurons. Indeed, augmenting the growth potential of centrally projecting axons via peripheral conditioning or other cAMP-dependent mechanisms improves axonal regeneration. Likewise, delivery of neurotrophins results in comparable gains. In addition to a limited growth capacity, an inhospitable extracellular environment hinders regeneration. Moderate microtubule stabilization increases the regeneration ability of axons at the same time that it decreases the inhibitory properties of scar tissue. Other therapeutic interventions that neutralize inhibitors associated with residual myelin or chondroitin-sulfate proteoglycan, a scar-associated inhibitor, also lead to improvements in axonal regeneration. Despite observations of only modest gains (~500 μm) using pharmacological therapies, neurons within the CNS can achieve long distance axonal regeneration.

After it was demonstrated that CNS axons have the ability to regenerate into PNS grafts, it has been found that long distance regeneration can be obtained using this approach. Within peripheral nerve grafts, parallel columns of Schwann cells surrounded by basal lamina (bands of Büngner) render excellent guidance to regenerating axons. However, harvesting autografts is limited by tissue availability and donor site morbidity, and the alternative acellularized allografts fail to support axonal regeneration. To mimic the favorable attributes of peripheral nerve grafts, several groups have used Schwann cells and topographic/chemotropic guidance cues to support regeneration. Nevertheless, poor survival limits the potential of cellular therapies, and neurotrophin administration requires precise timing, dose, and spatial distribution.

As such, there is currently no cure for spinal cord injury and there exists a need for scaffolds capable of promoting neural regeneration.

SUMMARY OF THE INVENTION

One aspect of the invention provides a three-dimensional scaffold including at least one layer of highly-aligned fibers. The at least one layer of highly-aligned fibers is curved in a direction substantially perpendicular to a general direction of the fibers.

This aspect of the invention can have a variety of embodiments. The fibers can be electrospun fibers. The fibers can be fabricated from one or more polymers. The one or more polymers can be selected from the group consisting of: poly-L-lactic acid (PLLA), polylactic-co-glycolic acid (PLGA), PLGA coated with polypyrrole, polycaprolactone, poly(ethersulfone), polytacrylonitrile-co-methylacrylate) (PAN-MA), and combinations thereof. The fibers can be biocompatible.

The three-dimensional scaffold can further include a base layer coupled to the fibers such that the base layer is also curved along one or more axes substantially parallel to a general direction of the fibers. The base layer can include a polymer film. The polymer film can be porous. The base layer can have a sufficient thickness to inhibit growth of neural axons through the base layer.

The three dimensional scaffold can further include a chemoattractant adjacent to the fibers. The chemoattractant can be laminin-1.

The at least one layer of highly-aligned fibers can be curved to form an S-shaped profile when viewed in a general direction of the fibers. The at least one layer of highly-aligned fibers can be curved to substantially define a conduit. The at least one layer of highly-aligned fibers can be curved to form an S-shaped profile within the conduit when viewed in a general direction of the fibers. The conduit can have an external diameter between about 2.0 mm and about 2.5 mm. The at least one layer of highly-aligned fibers can be curved to form a profile then viewed in a general direction of the fibers, the profile selected from the group consisting of: a C-shaped profile an I-shaped profile, a U-shaped profile, a W-shaped profile, and a Z-shaped profile.

The scaffold can have a length measured in the general direction of the fibers between about 1 mm and about 50 mm. The highly-aligned fibers can have a mean diameter between about 1.0 micron and about 1.2 microns.

In one embodiment, 84% of the highly-aligned fibers deviate no more than ±2° from a reference line parallel to the highly-aligned fibers. In another embodiment, 96% of the highly-aligned fibers deviate no more than ±2 from a reference line parallel to the highly-aligned fibers. In still another embodiment, 99% of the highly-aligned fibers deviate no more than ±2 from a reference line parallel to the highly-aligned fibers.

In one embodiment, 84% of the highly-aligned fibers deviate no more than ±5° from a reference line parallel to the highly-aligned fibers. In another embodiment, 96% of the highly-aligned fibers deviate no more than ±5° from a reference line parallel to the highly-aligned fibers. In still another embodiment, 99% of the highly-aligned fibers deviate no more than ±5° from a reference line parallel to the highly-aligned fibers.

In one embodiment, 84% of the highly-aligned fibers deviate no more than ±10 from a reference line parallel to the highly-aligned fibers. In another embodiment, 96% of the highly-aligned fibers deviate no more than ±10° from a reference line parallel to the highly-aligned fibers. In still another embodiment, 99% of the highly-aligned fibers deviate no more than ±10° from a reference, line parallel to the highly-aligned fibers.

Another aspect of the invention provides a method for fabricating a three-dimensional scaffold. The method includes: electrospinning a plurality of fibers to produce at least one layer of highly-aligned fibers and forming the at least one layer of highly-aligned fibers into a three-dimensional scaffold without disturbing the alignment of the highly-aligned polymer fibers.

This aspect of the invention can have a variety of embodiments. The plurality of highly-aligned fibers can be electrospun onto a base layer. The base layer can include a polymer film. The polymer film can be porous. The base layer can have a sufficient thickness to inhibit growth of neural axons through the base layer.

The fibers can be fabricated from one or more polymers. The one or more polymers can be selected from the group consisting of: poly-L-lactic acid (PLLA), polylactic-co-glycolic acid (PLGA), PLGA coated with polypyrrole, polycaprolactone, poly(ethersulfone), poly(acrylonitrile-co-methylacrylate) (PAN-MA), and combinations thereof. The fibers can be biocompatible.

The method can further include bonding one or more edges of the three-dimensional scaffold to maintain a shape of the three-dimensional scaffold. A PLLA/chloroform solution can be used to bond the one or more edges.

The method can further include applying a chemoattractant to the highly-aligned fibers.

The at least one layer of highly-aligned fibers can be curved to form an S-shaped profile when viewed in a general direction of the fibers. The at least one layer of highly-aligned fibers can be curved to substantially define a conduit. The at least one layer of highly-aligned fibers can be curved to form an S-shaped profile within the conduit when viewed in a general direction of the fibers.

The conduit can have an external diameter between about 2.0 mm and about 2.5 mm. The at least one layer of highly-aligned fibers can be curved to form a profile when viewed in a general direction of the fibers, the profile selected from the group consisting of: a C-shaped profile, an I-shaped profile, a U-shaped profile, a W-shaped profile, and a Z-shaped profile.

The scaffold can have a length measured in the general direction of the fibers between about 1 mm and about 50 mm. The highly-aligned fibers can have a mean diameter between about 1.0 micron and about 1.2 microns.

Another aspect of the invention provides a method of treating a peripheral nerve or spinal cord injury in a mammalian subject. The method includes: obtaining a three-dimensional scaffold having at least one layer of highly-aligned fibers and implanting the three-dimensional scaffold at the site of the peripheral nerve or spinal cord injury to induce regeneration of the peripheral nerve or spinal cord, thereby treating a peripheral nerve or spinal cord injury in a mammalian subject. The at least one layer of highly-aligned fibers is curved in a direction substantially perpendicular to a general direction of the fibers.

The three three-dimensional scaffolds described herein can further include a therapeutic agent. The therapeutic agent can be any therapeutic agent described herein. In embodiments, the therapeutic agent can be a polypeptide, polypeptide fragment, nucleic acid molecule, small molecule, ribozyme, shRNA, RNAi, antibody, antibody fragment, scFv, enzyme, carbohydrate, or combination thereof. The therapeutic agent can be paclitaxel. The therapeutic agent can be brain-derived neurotrophic factor (BDNF), neurotrophin-3 (NT3), nerve growth factor (NGF), or glial cell-line derived neurotrophic factor (GNDF). The therapeutic agent is chondroitinase ABC (chABC) or sialidase. The three-dimensional scaffold can release the therapeutic agent for at least 1 day, 1 week, or 1 month.

The three-dimensional scaffold can include a cellular substrate. The cellular substrate can be any cellular substrated described herein. In embodiments, the cellular substrate can be a schwann cell, an oligodendrocyte, an olfactory ensheathing glia (OEG), an oligodendrocyte progenitor cell (OPC), an embryonic stem cell (ESc), an adult stem cell, an induced pluripotent stem cell, a differentiated ESc and differentiated adult stem cell, an induced pluripotent Stem cell (iPSc), and a macrophage.

Another aspect of the invention provides a method of treating a mammalian subject by administering the three-dimensional scaffold as described herein to the subject.

Another aspect of the invention provides a method of treating a peripheral nerve or spinal cord injury in a mammalian subject by administering the three-dimensional scaffold as described herein to the subject.

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

DEFINITIONS

To facilitate an understanding of the present invention, a number of terms and phrases are defined below.

As used herein, the singular forms "a", "an", and "the" include plural forms unless the context clearly dictates otherwise. Thus, for example, reference to "a therapeutic agent" includes reference to more than one therapeutic agent.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," "treating," "treatment," and the like refer to reducing or ameliorating a disease or condition, e.g., CNS or PNS injury, and/or symptoms associated therewith. Moreover, treatment includes the partial or complete regeneration of nerve fibers in a subject. It will be appreciated that, although not precluded, treating a disease or condition does not require that the disease, condition, or symptoms associated therewith be completely eliminated.

As used C rein the term "central nervous system disease, disorder, or condition" refers to any disease, disorder, or trauma that disrupts the normal function or communication of the brain or spinal cord. The CNS and PNS injuries which can be treated according to the present invention are diverse and will be easily understood by the skilled person. Without limitation, there may be mentioned brain and spinal cord injuries due, to neurosurgery, trauma, ischemia, hypoxia, neurodegenerative disease, metabolic disorder, infectious disease, compression of the intervertebral disc, tumors, and autoimmune disease.

As used herein, the term "therapeutically active molecule" or "therapeutic agent" means a molecule, group of molecules, complex or substance administered to an organism for diagnostic, therapeutic, preventative medical, or veterinary purposes, This term includes pharmaceuticals, e.g., small molecules, treatments, remedies, biologicals, devices, and diagnostics, including preparations useful in clinical screening, prevention, prophylaxis, healing, imaging, therapy, surgery, monitoring, and the like. This term can also specifically include nucleic acids and compounds comprising nucleic acids that produce a bioactive effect, for example deoxyribonucleic acid (DNA), ribonucleic acid (RNA), or mixtures or combinations thereof, including, for example, DNA nanoplexes, ribozyme, shRNA, RNAi. The term also includes carbohydrates and polypeptides such as an antibody, antibody fragment, scFV, and enzymes. The term further includes radiotherapeutic agents; extracellular matrix components; free radical scavengers; chelators; antioxidants; anti-polymerases; photodynamic therapy agents gene therapy agents; and the like, Pharmaceutically active agents include but are not limited to any of the specific examples disclosed herein. Those of ordinary skill in the art will recognize also numerous other compounds that fall within this category and are useful according to the invention, Examples include a growth factor, e.g., nerve growth factor (NGF), brain-derived neurotrophic factor (BDNF), neurotrophin-3 (NT3), or glial cell-line derived neurotrophic factor (GNDF), a steroid, an anti-inflammatory agent, an analgesic agent, a sedative, a peptide agent, a biopolymeric agent, an antimicrobial agent, an enzyme (e.g., chondroitinase ABC (chABC) or sialidase), a protein, or a nucleic acid. In a further aspect, the pharmaceutically active agent can be steroids such as betamethasone, dexamethasone, methylprednisolone, prednisolone, precinisone, triamcinolone, budesonide, hydrocortisone, and pharmaceutically acceptable hydrocortisone derivatives; non-steroidal antiinflammatory agents, examples of which include but are not limited to sulfides, mesalamine, budesonide, salazopyrin, diclofenac, pharmaceutically acceptable diclofenac salts, nimesolide, naproxene, acetominophen, ibuprofen, ketoprofen and piroxicam, celocoxib, refocoxib, and N-[2-(cyclohexyloxy)-4-nitrophenyl]methanesulfonamide; analgesic agents such as salicylates; sedatives such as benzodiazapines and barbiturates: antimicrobial agents such as penicillins, cephalosporins, and macrolides, including tetracycline, chlortetracycline, bacitracin, neomycin, polymyxin, gramicidin, cephalexin, oxytetracycline, chloratriphenicol, rifampicin, ciprofloxacin, tobramycin, gentamycin, erythromycin, penicillin, sulfonamides, sulfadiazine, sulfacetamide, sulfatmethizole, solfisoxazole, nitrofurazone, sodium propionate, minocycline, doxycycline, vaticomycin, kanamycin, cephalosporins such as cephalothin, cephapirin, cetazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone; acids such as DNA sequences encoding for biological proteins and antisense oligonucleotides; and other pharmacological agents that have been shown to promote axonal regeneration such as paclitaxel (TAXOL®). The term also refers to combinations of any of the therapeutic agents disclosed herein, As used herein, the term "biological agent," "biological molecule," or "biological therapeutic" is intended to mean a subset of therapeutic agents that are a polypeptide or nucleic acid molecule, in specific embodiments, the biological therapeutic is an agent that induces or enhances nerve growth, e.g., a neurotrophic agent. Examples of useful neurotrophic agents are αFGF (acidic fibroblast growth factor), FGF (basic FGF), NGF (nerve growth factor), BDNF (brain derived neurotrophic factor), CNTF (ciliary neurotrophic factor), MNGF (motor nerve growth factor), NT-3 (neurotrophin-3), GDNF (glial cell line-derived neurotrophic factor), NT4/5 (neurotrophin4/5), CM101, (heat shock protein-27), IGF-I (insulin-like growth factory, IGF-II (insulin-like growth factor 2), PDGF (platelet derived growth factor) including PDGF-BB and PDGF-AB, ARIA (acetylcholine receptor inducing activity), LIF (leukemia inhibitory factor), VIP (vasoactive intestinal peptide), GGF (glial growth factor), and IL-1 (interleukin-1). In a preferred embodiment, the biological therapeutic is NGF or GNDF. In embodiments, the biological therapeutic is an antibody, antibody fragment, or scFV that induces or enhances nerve growth, e.g., an antibody specific for any of the neurotrophic agents described herein, in other embodiments, the biological therapeutic is a ribozyme, shRNA, or RNAi that induces or enhances nerve growth, e.g., an RNA molecule specific for any of the neurotrophic agents described herein.

As used herein, the term "scaffold" refers to a structure comprising a biocompatible material that provides a surface suitable for adherence and proliferation of cells. A scaffold may further provide mechanical stability and support. A scaffold be in a particular shape or form so as to influence or delimit three-dimensional shape or form assumed by a population of proliferating cells. Such Shapes or forms include, but are not limited to, films (e.g., a form with two-dimensions substantially greater than the third dimension), ribbons, cords, sheets, flat discs, cylinders, spheres, 3-dimensional amorphous shapes, etc.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymeric materials of the invention, biocompatible refers to the ability of the polymeric material for polymeric materials) to be accepted by and to function in its intended manner in a recipient.

As used herein, "therapeutically effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with a particular disease or disorder. A physician or veterinarian of ordinary skill can readily determine and prescribe the effective amount of the bioactive agent required to treat and/or prevent the progress of the condition.

Unless specifically stated of obvious from contest, as used herein, the term "about" is understood, as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0,01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compounds, compositions, or methods provided herein can be combined with one or more of any of the other compositions and methods provided herein.

DESCRIPTION OF THE DRAWINGS

FIG. 1A shows the image of the custom electrospinning apparatus that was used to generate aligned polymeric fibers. FIG. 1B depicts coverslips being mounted on a grounded target. A rotation speed of 1500 rpm was used to align fibers produced by a 15 kV field potential. Random fibers were generated using a stationary target. For conduit assembly, films with or without electrospun fibers were peeled from coverslips (FIG. 1C), placed back to back (FIG. 1D), and rolled (FIG. 1E) into conduits (FIG. 1F).

FIGS. 2A-2C include images of isolated DRG from P4 rat pups cultured on film (FIG. 2A), random (FIG. 2B), and aligned fiber (FIG. 2C) substrates. FIGS. 2D and 2E include images from scanning electron microscopy of random (FIG. 2D) and aligned (FIG. 2E) polymer fibers. FIGS. 2F-H include graphs. The eccentricity (FIG. 2F), a measure of anisotropy, and the maximum (FIG. 2G) and average (FIG. 2H) distance reached by neurites were quantified on DRG explants. Markedly, aligned polymer fibers elicited linear neurite elongation, providing an efficient means of growth as demonstrated by a significant increase in the maximum and average distance reached by neurites over the same time in culture. F, film; R, random; A, aligned. Data are mean±SEM; n=6, *P<0.05 by ANOVA. Scale bars: 500 µm in FIGS. 2A-2C and 50 µm in FIGS. 2I and 2E.

FIGS. 3A and 3C include include images from scanning electron microscopy of random (FIG. 3A) and aligned (FIG. 3B) fibers. FIGS. 3B and 3D include graphs showing the results alignment quantification as measured by the angle between a given fiber and the median fiber orientation for 150 fibers per condition. FIG. 3E includes an image from scanning electron microscopy and FIG. 3F includes a graph showing the alignment quantification results. The results demonstrate that fiber alignment was maintained through the process of conduit assembly FIG. 3B includes an image of the macroscopic view of aligned fiber conduit lumen, by mounting a conduit sectioned on the longitudinal axis, FIG. 3H includes an image showing the coronal view of an aligned fiber conduit, The diameter of all conduits was 2.6 mm. Scale bars: 50 µm in FIG. 3A: 100 µm in FIGS. 3C and 3E; and 1 mm in FIGS. 3D and 3H.

FIG. 4E includes an image of the spinal cord with a film conduit 1 week after implantation. FIG. 4F includes an image of the spinal cord with an aligned conduit 4 weeks after implantation. Tissue is visible within the conduit lumen at 4 weeks. (Scale gradation, 1 mm).

FIGS. 5A-5E include images of cresyl violet and DAPI tissue overviews, FIGS. 5A, 5D, and 5G include representative images of cresyl violet iota ne d spinal cord sections for film fiber conduits. FIGS. 5B, 5E, and 5H include representative images of cresyl violet stained spinal cord sections for random fiber conduits. FIGS. 5C, 5F, and 5I include representative images of cresyl violet stained spinal cord sections for aligned fiber conduits. FIGS. 5J-5L include representative images of DAPI overviews for film (FIG. 5J), random (FIG. 5K), and aligned (FIG. 5L) fiber conduits at 4 weeks. Random and aligned fibers support gap closure by host cells at 4 weeks, visualized here by the presence of Niss1 bodies and DAPI nuclear counterstain. Large cavities are observed at the rostral and caudal graft interfaces of film conduits after 4 weeks (FIGS. 5G and 5J). (Scale bar, 1 mm), FIGS. 6A-6C include representative images of cresyl violet staining 4 weeks after implantation of film (FIG. 6A), random (FIG. 6B), and aligned fiber (FIG. 6C) conduits. The results demonstrate that both random and aligned fibers support tissue integration into conduits and limited cavitation in host cord tissue. FIG. 6D includes a graph of tissue volume inside conduits at 1, 2, and 4 weeks post-injury as measured by a Cavalieri estimator probe. Both random and aligned fiber conduits had significantly more endogenous tissue than film conduits at 4 weeks. Data are mean±SEM: n=3 (1 W, 2 W), n=7 (4 W). *P<0.05 by ANOVA. (Scale bar, 1 mm.)

FIG. 7C includes an immunostaining image for laminin in the basement membrane of blood vessels. A distinct difference in the pattern of angiogenesis is observed between the rostral and caudal spinal cord. In the rostral spinal cord, blood vessel formation occurs in close proximity to the regeneration front. Scale bars: 500 µm in (FIG. 7A); 50 µm in (FIG. 7B); 100 µm in (FIG. 7C).

FIGS. 8A, 8D, and 8G include representative images of horizontal spinal cord sections for film fiber conduits. FIGS. 8B, 8E, and 8H include representative images of horizontal spinal cord sections for random fiber conduits. FIGS. 8C, 8F, and 8I include representative images of horizontal spinal cord sections for aligned fiber conduits. Aligned fibers foster robust time-dependent rostrocaudal axonal regeneration (FIGS. 8C, 8F, and 8I), whereas the same response is absent in film and random fiber conduits. FIGS. 8J and 8K include graphs showing quantitative results from the immunostains. The distance between the rostral edge of the conduit to the axonal front was quantified at all time points (FIG. 8J). Remarkably, over 4 weeks aligned fibers promote robust, long distance regeneration (2055±150 µm), significantly greater than random fiber (1162±87 µm) and film (413±199 µm) controls. Notably, at 4 weeks, 100% (7/7) of the animals rom the aligned fiber group had a robust regeneration response present in the middle of the conduit compared to 14.3% (1/7) and 0% (0/6) in the random fiber and film groups, respectively (FIG. 8K). FIGS. 8L includes in immunostain showing that serotonergic ($5HT^+$) axons were abundant in the robust growth observed inside aligned conduits (inset from adjacent section of the same animal in I). FIG. 8M includes in immunostain showing that serotonergic axons were present caudal to the graft in 3/21 animals (2 random, 1 aligned fiber). Data are mean±SEM; n=3 (1 W, 2 W), n=6-7 (4 W). *$P<0.05$ by ANOVA. Scale bars: 1 mm in (FIGS. 8A-8I); 150 µm in (FIG. 8L); 50 µm in (FIG. 8M).

FIGS. 10A, 10D, and 10G include representative GFAP stains of horizontal spinal cord sections for film fiber conduits. FIGS. 10B, 10E, and 10H include representative GFAP stains of horizontal spinal cord sections for random fiber conduits. FIGS. 10C, 10F, and 10I include representative GFAP stains of horizontal spinal cord sections for aligned fiber conduits. Both random and aligned fibers support a time dependent migratory response of astrocytes (FIGS. 10B, 10C, 10E, 10F, 10H, and 10I), whereas dependent astrocytic dieback is observed in film conduits. Figure J (inset front Figure I) includes an image of double-labeling for GFAP and RT97. The results indicate that axonal regeneration is localized to astrocytes migrating from the rostral spinal, cord. FIGS. 10K and 10L are high-magnification confocal micrographs (inset from Figure J) showing morphologically aligned migrating astrocytes in close proximity to regenerating axons. Scale bars: 1 mm in (FIGS. 10A-10I); 500 µm in (FIG. 10J); 50 µm in (FIGS. 10K and 10L).

FIGS. 12A and 12C include images of cresyl violet staining in sections adjacent to GFAP/RT97 stained sections The results demonstrate that polymer fibers guide rostrocaudal growth in random (FIG. 12A) and aligned fiber (FIG. 12C) conduits. Black arrowheads point to polymer fibers, random fibers in (FIG. 12A) project orthogonal to the plane of the tissue section, whereas aligned fibers (FIG. 12C) remain in the plane of the section. FIGS. 12B and 12D include images showing that after 4 weeks, astrocytes (GFAP) and regenerating axons (RT97) enter random (FIG. 12B) and aligned fiber (FIG. 12D) conduits in close proximity, and axons lead the response. White arrowheads point to axons at the regeneration front, (Scale bar, 500 µm).

FIG. 13A includes an image of a histological section of whole spinal cord 8 weeks after implantation of a conduit without fibers. FIG. 13B includes an image of a histological section of whole spinal cord 8 weeks after implantation of a conduit with fibers. The results demonstrate that the presence of fibers within the conduit allowed for better tissue integration into the conduit. FIG. 13C-13F include immunostains showing that blood vessels were within the conduits after 4 weeks (FIG. 13C) and astrocytes (FIG. 13D) entered the conduit with fibers 8 weeks after implantation. Few neurons were in conduits without fibers (FIG. 13E), but when fibers were present (FIG. 13F), robust axonal ingrowth occurred 8 weeks post-implantation. Dashed lines denote conduit wall structure.

DETAILED DESCRIPTION OF THE INVENTION

Figure 1A:
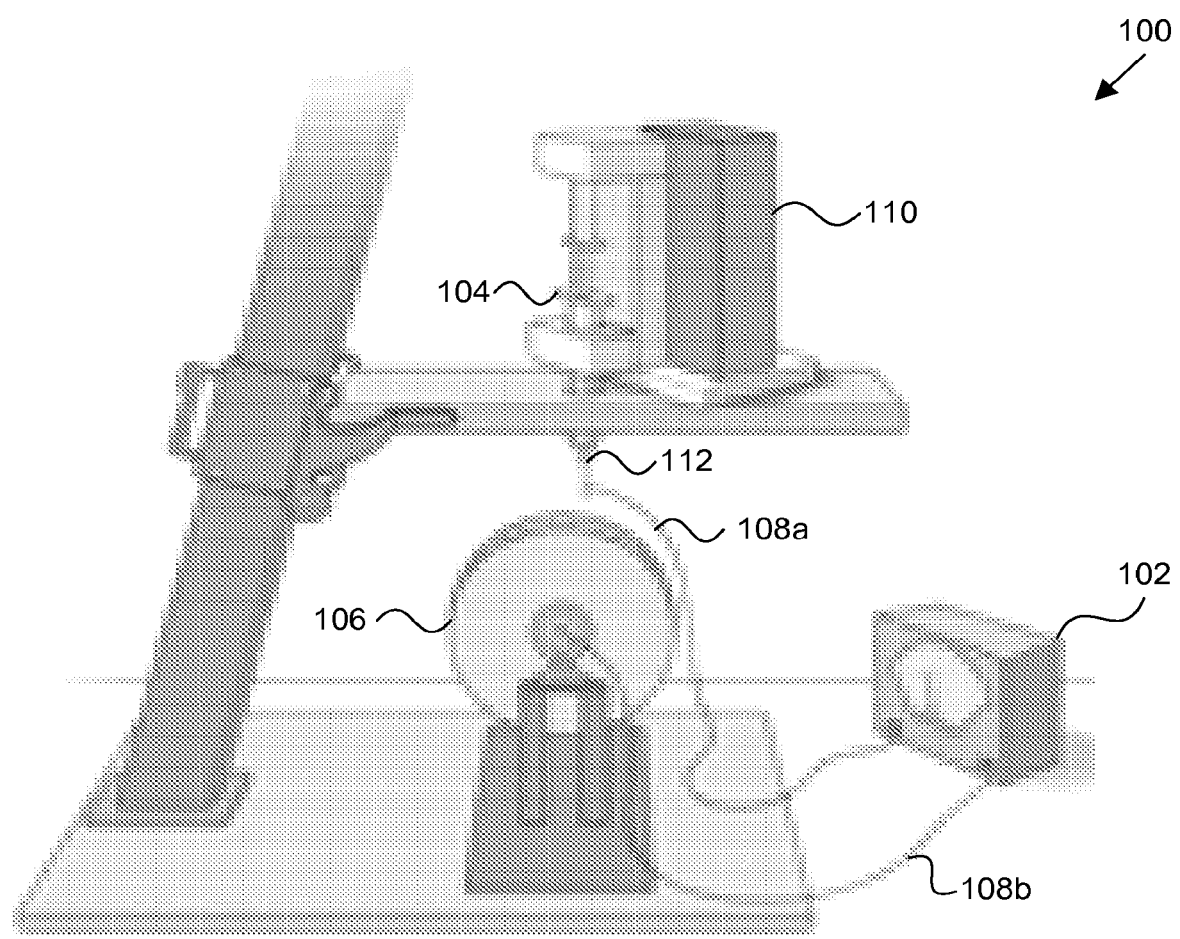
FIGS. 1A-1F include a schematic detailing the materials fabrication process.

It has previously been shown that aligned, electrospun fibers are supportive to neural cell growth. Dorsal root ganglia, neural stem cells, Schwann cells, and neuroblastoma cells have been investigated on PLLA (Wen and Tresco, *J. Biomed. Mater. Rev. A* 76A:626-637 (2006): Yang et al., *Biomaterials* 26; 2603-2610 (2005); Yang et al., *J. Biomater. Sci. Polym. Ed.* 15:1483-1497 (2004); and Corey et al., *J. Biomed. Mater. Res.* 83:636-645 (2007)), PLGA (Bini et al., *J. Mater. Sci.* 41:6453-6459 (2006)), and poly-ε-caprolactone fibers (Schnell et al., *Biomaterials* 28:3012-3025 (2007)). However, most of these studies focused on 2D scaffolds with random or aligned fiber orientation and evaluated the influence of the scaffolds in vitro. Thus, further development of novel implantable 3D electrospun fibrous scaffolds for neural tissue engineering applications is necessary, A variety of three-dimensional constructs have also been investigated; however, 3D scaffolds have been employed with variable success for both CNS and PNS nerve regeneration. One example includes a freeze-dried agarose with uniaxial channels for spinal cord injury (Stokols and Tuszynski, *Biomaterials* 27:443-451 (2006)). A 2D-like substrate/surfaces in 3D space has also been suggested. For example, a 'Z' shape of aligned fibers within a three dimensional conduit has been used for peripherals nerve regeneration (Bellamkonda et al., *Biomaterials* 27:3515-3518 (2006)). 3D hydrogel matrices with capillaries or channels (Prang et al,. *Biomaterials* 27:3560-3569 (2006); and Luo et al., *Nat. Mater.* 3:249-253 (2004)) and fibers/filaments scaffolds (Evans et al., *Biomaterials* 23:841-848 (2002); and Cai et al., *J. Biomed. Mater. Res. A* 75:374-386 (2005)) have also been fabricated for spinal cord injury. Other research models of electrospinning conduits as a blood vessel substitute have been reported (Stitzel et al., *Biomaterials* 27:1088-1094 (2006); and Vaz et al., *Acta Biomater.* 1:575-582 (2005)), but loss of alignment of the fibers limits its potential for neural tissue engineering applications. in addition, three dimensional constructs containing aligned fibers have been constructed previously for peripheral nerve, regeneration models (Kim et al., *Biomaterials* 29:3117-3127 (2008); and Chew et al., *Adv. Funct. Mater.* 17:1288-1296 (2007)). However, fiber alignment was not optimized and the process to make the conduit is complicated. Therefore, an ideal 3D, biomaterial scaffold that satisfies all the general characteristics of facilitating complete regeneration within the peripheral nervous system or the spinal cord remains elusive.

This present invention is based, at least in part, on the discovery of an aligned microfiber-based synthetic polymer substratum that promotes robust CNS tissue growth without neurotrophin administration or cell transplants. The invention includes a multilayer three dimensional poly(L-lactic acid) (PLLA) conduit consisting of double sided aligned electrospun fibers. By implanting the biodegradable conduits with aligned microfibers in an acute complete transection rat model of spinal cord injury, the inventors discovered that topographic cues provided by aligned poly(L-lactic acid) (PLLA) microfibers promote axonal regeneration within the CNS. This is the first example of taking highly aligned fibers and placing them into a three dimensional scaffold without disturbing fiber alignment. Compared to aforementioned scaffolds, several properties make the present multilayer 3D conduit a superior candidate for nerve repair and regeneration applications clinically, first, the novel wall structure made of double-sided fibers increases the opportunities for cell migration. The only material used is the biodegradable material PLLA, which reduces the immunogenic risk. In addition, the walls have two important characteristics: i) the thin films are not rigid, which makes them less likely to cause additional damage to the cord, and ii) the thin films provide adequate mechanical support after implantation. Also, the unique "I" shape center line design provides enough space for regenerating neurons to penetrate the fiber channels, while at the same time providing an increased surface area of contact for regenerating axons. Furthermore, the high ratio of surface area to volume of electrospun fibers make the conduit a suitable reservoir for drug delivery to enhance nerve, regeneration. What is more, since the fibers were electrospun on a movable film, it is possible to make many kinds of inner designs such as a helical shape, "U" shape, or "Z" shape based on different applications. The conduit is easy to fabricate, and the dimensions of the scaffold can be manipulated to fit injuries of different geometry.

Accordingly, the invention provides for three-dimensional scaffolds, methods of fabricating three-dimensional scaffolds, and methods for treating a peripheral nerve or spinal cord injury.

Fabrication of Three-Dimensional Scaffolds

One embodiment of the invention provides a biocompatible implantable layered 3D scaffold. Examples of such methods and materials are provided below, and one of ordinary skill in the art will be familiar with all equivalent variations in methodology and materials well-known in the art.

The 3D scaffolds of the present invention are biocompatible and biodegradable. The conduit offers several advantages as a novel nerve guidance scaffold. First, highly-aligned fibers direct axonal extension. The conduit consists of a bilayer of ELLA films covered with aligned, electrospun fibers, which enhance neuronal attachment and guide axonal extension in a directed manner. Second, alignment of the fibers is maintained during the fabrication process. Third, the thin layer wall structure provides adequate mechanical support, but prevents axons from growing through the wall. Importantly, the parameters of the conduit are variable and desired length, luminal structure, diameter, and even the orientation of the fibers can be modified according to different applications.

Referring now to FIG. 1A, an electrospinning apparatus 100 for fabricating aligned fibers (e.g., PLLA fibers) is provided. A high-voltage power supply 102 (available from Gamma High Voltage Research of Ormond Beach, Fla.) provides a charge differential between a syringe 104 and a rotating collector 106 via wires 108a, 108b. A multi-speed syringe pump 110 (available from Braintree Scientific of Braintree, Mass.) is positioned perpendicularly to the ground.

Syringe 104 can be a glass syringe (e.g., a 5.0 ml glass syringe). Syringe 104 includes a needle 112. Various needles 112 can be utilized to achieve desired fiber characteristics. Suitable needles 12 include 200 flat and sharp tip needles having an inner diameter of 0.6 mm and a 22G sharp-tip needle with an inner diameter of 0.4 mm. All three needles are available from Fisher Chemicals of Fair Lawn, N.J. Wire 108a, can be connected directly to needle 112 to charge a polymer solution within syringe 104 as depicted in FIG. 1A. Alternatively, needle 112 can be insulated to increase electrospinning efficiency. Needle 112 can be insulated by applying tubing (e.g., MASTERFLEX® or TYGON® tubing available from Fisher Scientific of Pittsburgh, Pa.) over needle 112.

A solution is loaded within syringe 104. For example, an 8% by weight solution of PLLA dissolved into 1:1 chloloform and dichloromethane mixed solvent can be loaded into syringe 104 to produce electrospun PLLA fibers.

Rotating collector 106 is a rotating disk (e.g., 220 mm in diameter with a thickness of 10 mm) attached to a laboratory mixer motor (available from IKA Works Inc. of Wilmington, N.C.). Rotating collector 106 can rotate at a variety of speeds including 250 RPM (linear distance=172.7 cm/min), 500 RPM (linear distance=345.4 cm/min), and 1000 RPM (linear distance=690.8 cm/min).

To produce electrospun fibers, a charge (e.g., about 15 kV or about 20 kV) is applied to syringe 104, rotating collector 106 is spun, and syringe pump 110 is actuated (e.g., to achieve a flow rate of about 1 mL/hour). In some embodiments, the distance between the tip of needle 112 is about 5.5 cm. Fibers can be collected for a variety of durations (e.g., about 45 minutes or about 1 hour). Electrospinning apparatus 100 can be operated in a variety of environmental conditions (e.g., at a temperature of about 26° C. and constant relative humidity of about 58%).

Figure 1B:
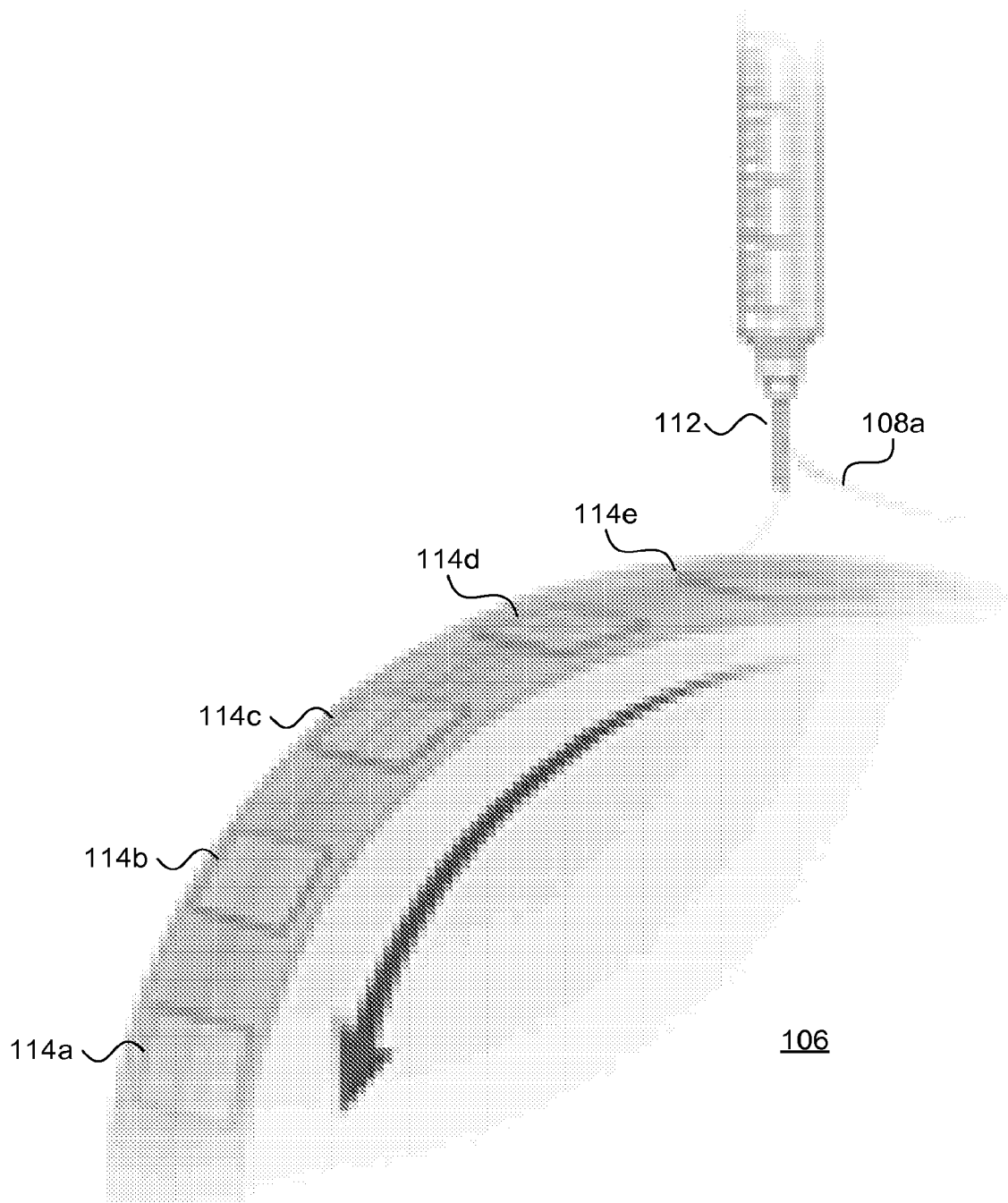

Referring now to FIG. 1B, a plurality of glass coverslips 114 are coupled to the outer perimeter of rotating collector 106, for example, with double-side tape available from 3M of St. Paul, Minn.). Glass coverslips can have a variety of dimensions such as about 12-by-12 mm. Electrospun fibers 116 are dispensed from needle 112 onto coverslips 114 as rotating collector 106 spins, thereby forming a plurality of electrospun fibers aligned in the rotational direction of the rotating collector 106.

Figure 1C:
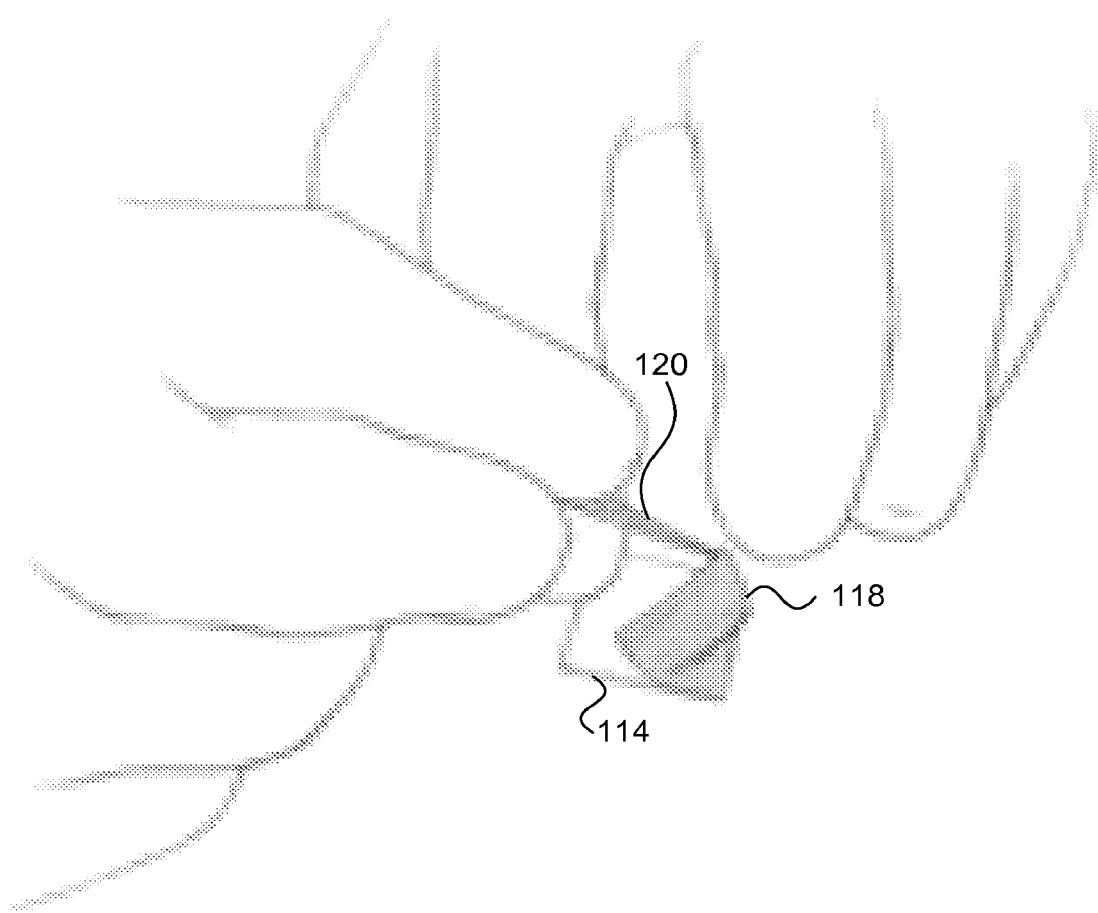

Referring now to FIG. 1C, a layer of electrospun fibers can be removed (e.g., manually or using implements such as tweezers 120) from coverslip 114. In some embodiments, the layer 118 are placed in a fume hood overnight at room temperature to eliminate any residual solvent.

Figure 1D:
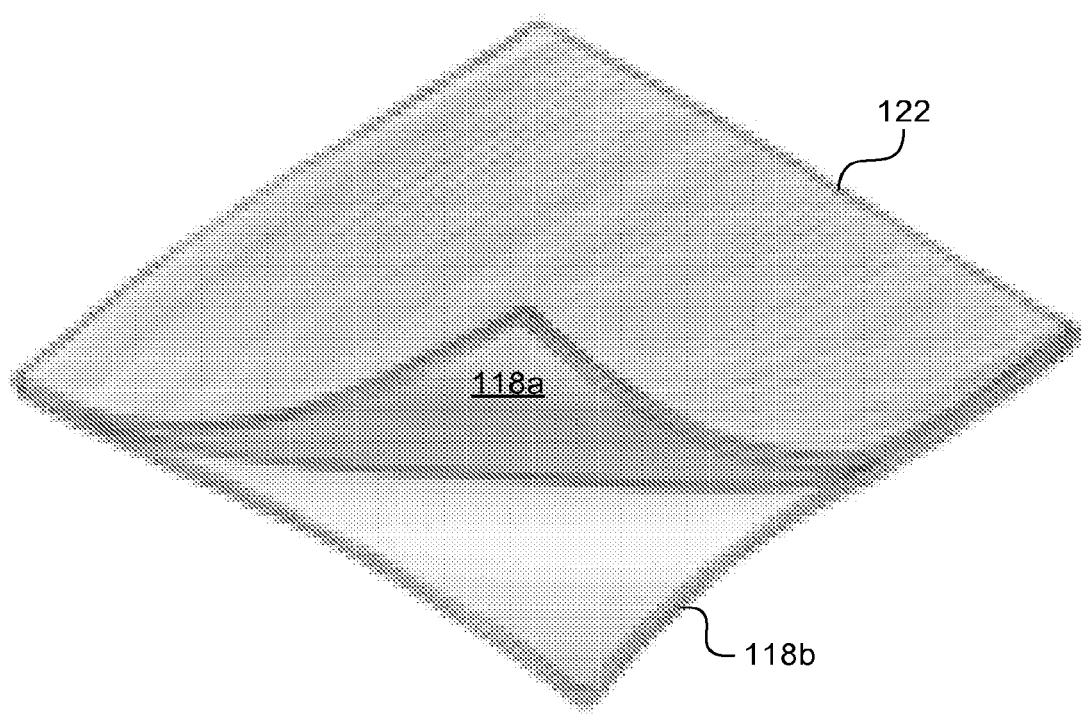

Referring, now to FIG. 1D, two layers 118a, 118b of electrospun fibers can be bonded together to produce a double sided film 122. Films 118a, 118b can be adhered by static for because the thickness of the films 118a, 118b is very small between about 10 microns and about 30 microns and generally having an average thickness of about 20 microns).

Figure 1E:
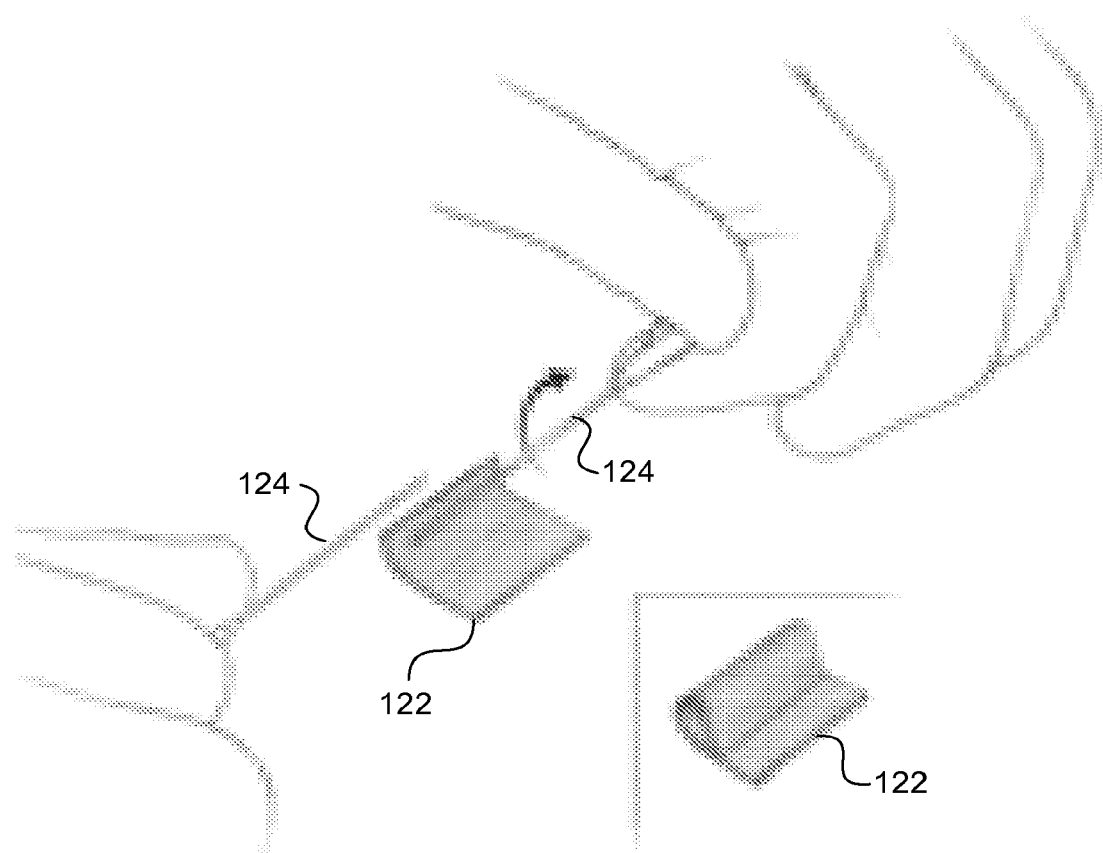

Referring now to FIG. 1E, the assembled double-sided film 122 can then be rolled, folded, and/or otherwise manipulated to form a three-dimensional scaffold. The doubled-sided film 122 can be manipulated using various implements such as tweezers having slit cut to receive the double-sided film 122.

Figure 1F:
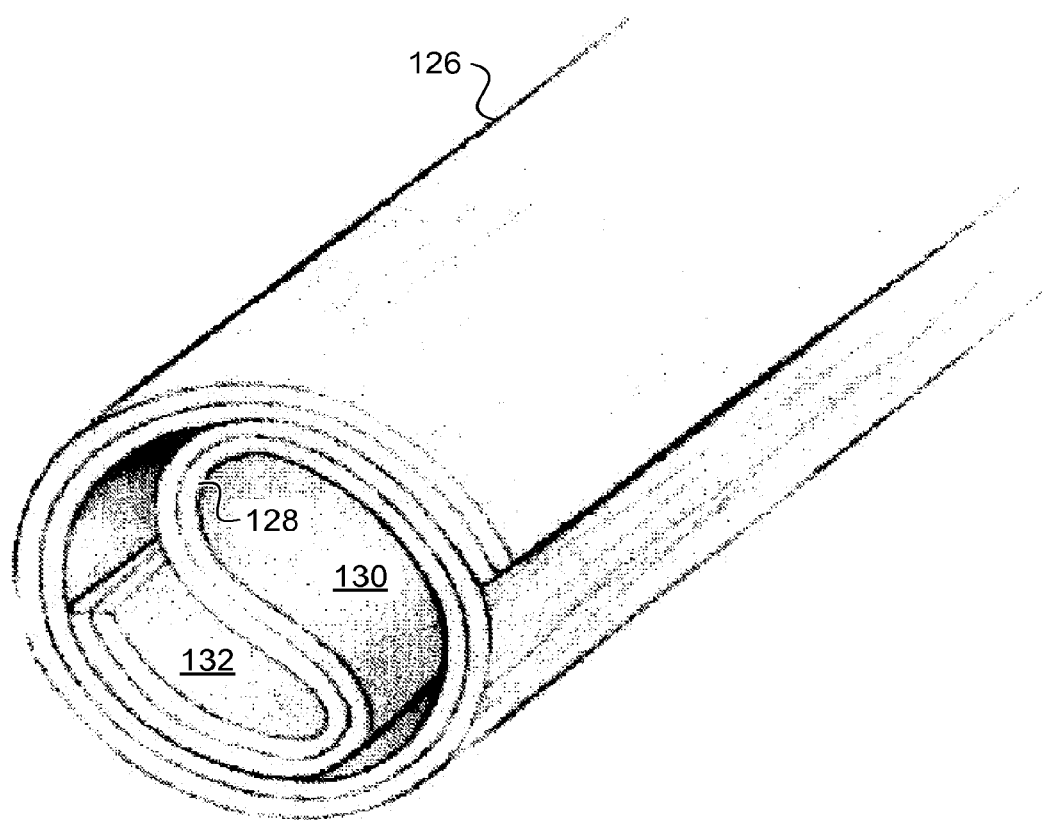

Referring now to FIG. 1F, a perspective view of as assembled three-dimensional scaffold 126 is provided. A variety of different three-dimensional geometries can be achieved using the material and methods provided herein. In the particular embodiment of the three-dimensional scaffold 126 depicted in FIG. 1F, the scaffold 126 has a substantially cylindrical profile with an internal 'S'-curve 128 that defines a first channel 130 and a second channel 132.

The assembled scaffold can have various lengths designed for implantation in various anatomical locations in various subjects. For example, the scaffold can have a length measured in the general direction of the fibers between about 1 mm and about 50 mm. Longer scaffolds (e.g., having lengths up to about 10 cm) can be fabricated by utilizing larger slide covers or by coupling multiple swatches of electrospun fibers using a PLLA/chloroform solution).

In general, the scaffolds are formed from at least one layer of highly-aligned fibers. As discussed herein, the highly-aligned fibers can be produced by electrospun fibers. The fibers can be a variety of materials, preferably biocompatible materials, such as polymers, protein fibers (e.g., collagen, gelatin (denatured collagen), elastin), metals, and the like, in one embodiment. the fibers are polymer fibers. For example. the one or more polymers can be selected from the group consisting of PLLA, PLGA, PLGA coated with polypyrrole, polycaprolactone, poly(ethersulfone), poly(acrylonitrile-co-methylacrylate) (PAN-MA), and combinations thereof (e.g., a combination of PLLA and PLGA). Mixtures polymers can be formed in the liquid phase prior to electrospinning or can be formed by electrospinning a plurality of different polymer fibers.

The highly-aligned fibers have a variety of dimensions. For example, the fibers can have a mean diameter between about 0.5 microns and about 2.0 microns, between about 1.0 micron and about 1.5 microns, between about 1.0 micron and about 1.2 microns, and the like.

The three-dimensional scaffolds are formed by curving the at least one layer of highly-aligned fibers along in a direction substantially perpendicular to a general direction of the fibers. As a result, the fibers remain substantially unbent and the three-dimensional scaffold can have a generally-cylindrical geometry such that any cross-section perpendicular to the general direction of the fibers has a substantially similar geometry.

In some embodiments, the highly-aligned fibers are formed on a base layer. The base layer can include a polymer film. The polymer film can, in some embodiments, be a biocompatible polymer such as PLLA, PLGA, PLGA coated with polypyrrole, polycaprolactone, poly(ethersulfone), poly(acrylonitrile-co-methylacrylate) (PAN-MA), and combinations thereof (e.g., a combination of PLLA and PLGA). The polymer film can be formed from various known fabrication methods including solution casting, molding, extrusion, and the like.

In some embodiments, the base layer has a sufficient thickness to inhibit growth of neural axons through the base layer. For example, the base layer can have a thickness greater than about 1 micron, about 10 microns, about 20 microns, and like.

In still other embodiments, the base layer is semi permeable so as to allow for diffusion of nutrients across the scaffold.

A chemoattractant such as laminin-1 can be placed adjacent to the highly-aligned fibers to promote growth of neural axons upon implantation. For example, the chemoattractant can be applied to the outer surface(s) of the highly-aligned fibers, placed between the highly-aligned fiber layer and the base layer, and/or incorporated within the base layer.

Referring to FIG. 14, various architectures for three-dimensional scaffolds are provided. For example, as three-dimensional scaffolds can have a S-shaped profile as depicted in FIG. 14A, a C-shaped profile as depicted in FIG. 14B, an O-shaped profile as depicted in FIG. 14C, a U-shaped profile as depicted in FIG. 14D, a W-shaped profile as depicted in FIG. 14E, a Z-shaped profile as depicted in FIG. 14F, an I-shaped profile as depicted in FIG. 14G, and a helicoid within a conduit as depicted within FIG. 14H, and the like. The various profiles provides can be enclosed by further wrapping of the highly-aligned fibers to form a substantially-circular outer profile.

In FIGS. 14A-14F, the solid lines denote the outer boundaries of the highly-aligned fiber layers. The dashed lines denote the boundary between the highly-aligned fiber layers, which may include a base layer and/or a chemoattractant in some embodiments.

Figure 15:
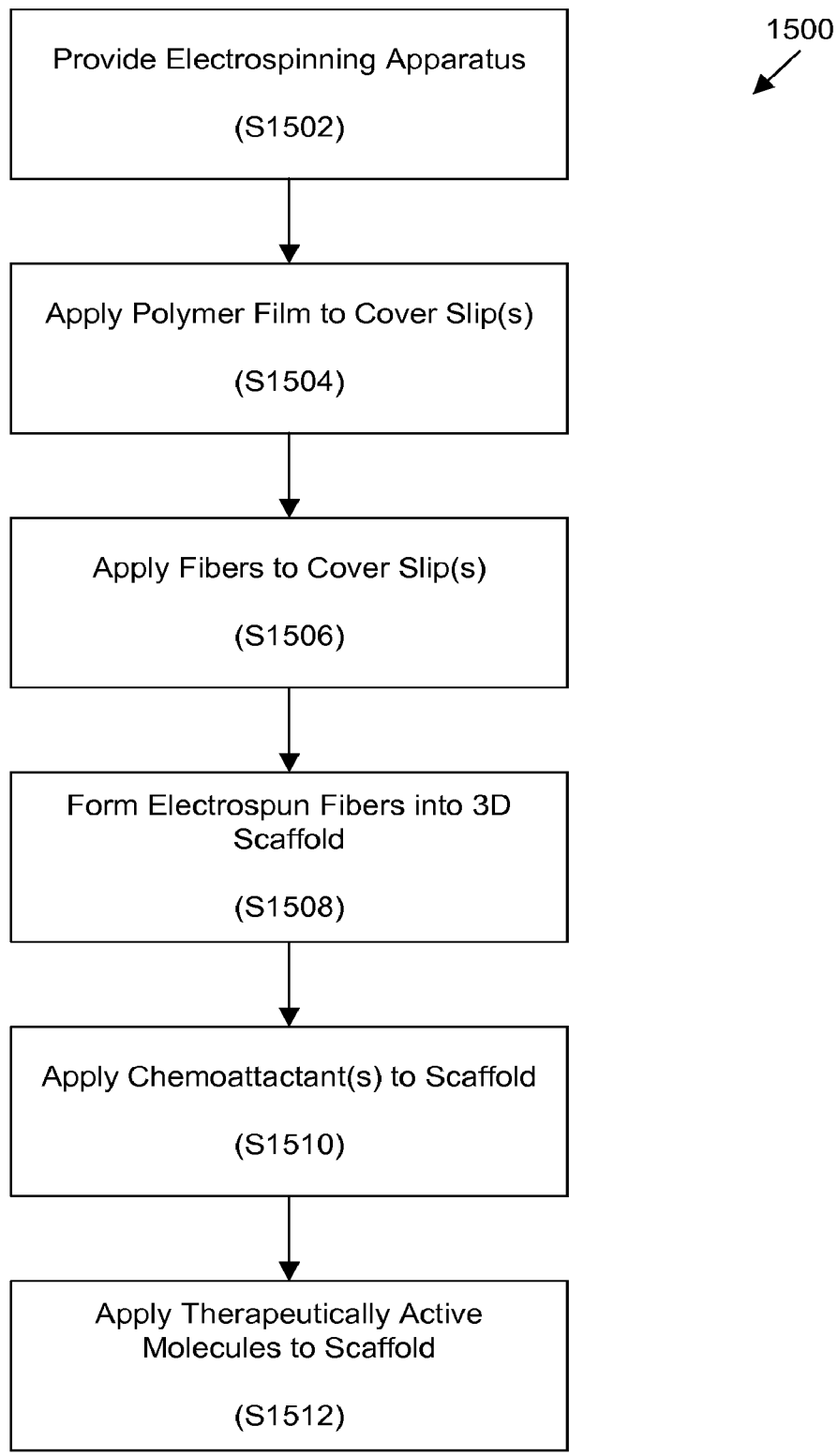
FIG. 15 depicts a method of fabricating a three-dimensional scaffold according to an embodiment of the invention.

Referring now to FIG. 15, a method 1500 of forming a three-dimensional scaffold is provided.

In step S1502 electrospinning apparatus is provided. The electrospinning apparatus can be a commercially-available electrospinning apparatus or can be custom-made. The electrospinning apparatus can, in some embodiments, be an electrospinning apparatus as described herein. For example, the electrospinning apparatus can include one or more cover slips or other plates on a rotating collector.

In step S1504, a polymer film is optionally applied to the one or more cover slips. The polymer film can be applied to the cover slips using various techniques at solution casting, extrusion, molding, physical vapor deposition, thin film deposition, and the like. Preferably, the polymer film can be easily removed from the cover slip. One or more release agents can optionally be applied to the cover slip before the polymer is applied to ease the later removal of the polymer film.

In step S1506, a plurality of fibers are electrospun onto the cover slip and the optional polymer film as discussed herein.

In step S1508, the electrospun fibers are removed from the cover slip along with the optional polymer In step S1508, electrospun fibers are formed into a three-dimensional scaffold. Although forming as described herein has been accomplished manually and with hand tools such as tweezers, one of ordinary skill in the art will appreciate that three-dimensional scaffolds can be formed using automated machinery and processes.

In step S1510, chemoattractants such as laminin-1 can be optionally applied to the three-dimensional scaffold.

In step S1512, one or more therapeutic agents can be optionally applied to the three-dimensional scaffold to promote nerve growth, reduce swelling, and the like.

Therapeutic Agents

The invention also provides scaffolds comprising, one or more therapeutic agents.

In embodiments, one or more therapeutic agents are provided as a filling inside the conduit. Suitable fillings for carrying therapeutic agents are well-known in the art, e.g., a hydrogel In embodiments, one or more therapeutic agents are incorporated into the film or fiber during fabrication. In embodiments, one or more therapeutic agents are incorporated into the film and the fiber during fabrication. In related embodiments, the same therapeutic agent is incorporated into the film and the fiber. In other embodiments, different therapeutic agents are incorporated into the film and the fiber during fabrication. Methods for incorporating therapeutic agent(s) into film and/or fiber are well-known in the art. See, et al., *Adv. Funct. Mater.* 17:1288-96 (2007), which is incorporated by reference.

The fiber and/or film may comprise about 0.01. 0.05, 0.1, 0.5, 1, 2, 3, 4, 5, 6, 7, 8, 9, 10, 11, 12, 13, 14, 15, 16, 17, 18, 19, or 20 of the therapeutic agent by weight of the fiber and/or film. In embodiments, the therapeutic agent comprises about 1-20%, 1-10%, or 1-5% of the fiber and/or film by weight. One of skill in the art will readily appreciate that different amounts of therapeutic agent(s) can be delivered to a subject by varying the amount o the polymeric fiber in the conduits of the invention.

In embodiments, the therapeutic agent is immediately released from the filling (e.g., hydrogel), fiber, and/or film.

The conduits of the invention are also effective at delivering a therapeutic agent to a subject in need thereof over a prolonged period of time. For example, the conduits of the invention may release therapeutic agent(s) for periods of 1 day to 18 months, Specifically, the conduits of the invention release therapeutic agent(s) for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 45 days, 60 days, 90 days, 120 days, 180 days, 360 days, or more.

Rate of release depends on degradation of the polymer and the solubility of the therapeutic agent. One of skill in the art can readily select the polymer and fabrication method needed to deliver a specific therapeutic agent at a desired rate of release. In general, the therapeutic agent is released as the scaffold degrades. Thus, a slow-degrading polymer will generally release a therapeutic agent for a relatively longer period of time, but at a relatively lower rate. Conversely, a fast-degrading polymer will generally release a therapeutic agent for a relatively shorter period of time, but at a relatively higher rate. In embodiments, the therapeutic agents) can be encapsulated in materials well-known in the art to control the rate of release of the therapeutic agent(s). In embodiments, the therapeutic agent(s) are incorporated into the electrospun fibers and/or films (see WO 2007/089259, which is hereby incorporated by reference). In related embodiments, the density of the electrospun fibers can be adjusted by one of ordinary skill in the art to increase or decrease the length of time that therapeutic molecules are released from the composition. Moreover, varying the density of the electrospun fiber composition can be used to modulate the amount of the therapeutic agent that is released per unit of time Exemplary therapeutic agents include biological agents and small molecules, For example, therapeutic agents include, but are not limited to, neuropathic agents; neurotrophic agents; antimicrobial agents, such as antibiotics (e.g., tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephaparin, cefazolin, cephalexin, cephardine, cefadroxil, cefamandole, cefoxitin, cefaclor, cefuroxime, cefonicid, ceforanide, cefitaxime, moxalactam, cetizozime, ceftriaxone, cefoperazone), anti-inflammatories such as aspirin (salicylic acid), indomethacin, sodium indometbacin trihydrate, salicylamide, naproxen, colchicine, fenoprofen, sulindac, diflunisal, diclofenac, indoprofen and sodium salicylamide; steroids such as betamethasone, dexamethasone, methylprednisolone, prednisolone, prednisone, triamcinolone, budesonide, hydrocortisone, and pharmaceutically acceptable hydrocortisone derivatives; non-steroidal anti-inflammatories such as salicylate, indomethacin, ibuprofen, diclofenac, flurbiprofen, piroxicam, celocoxib, refocoxib, and N-[2-(cyclohexyloxy)-4-nitrophenyl]-methanesulfonamide; analgesic agents such as salicylates; sedatives such benzodiazapines and barbiturates; immunosuppressive agents, growth factors such as NGF or GNDF; peptides; proteins; enzymes; nucleic acids and nucleic acid fragments, gene therapy agents; and the like.

In embodiments, the therapeutic agent is as neurotrophic agent. Exemplary neurotrophic agents include, but are not limited to, αFGF (acidic fibroblast growth factor), βFGF (basic FGF), NGF (nerve growth factor), BDNF (brain derived neurotrophic factor), (ciliary neurotrophic factor), MNGF (motor nerve growth factor), N-3 (neurotrophin-3), GDNF (glial cell line-derived neurotrophic factor), NT4/5 (neurotrophin4/5), CM101, HSP-27 (heat shock protein-27), IGF-I (insulin-like growth factor), IGF-II (insulin-like growth factor 2), PDGF (platelet derived growth factor) including PDGF-BB and PDGF-AB, ARIA (acetylcholine receptor inducing activity), LIF (leukemia inhibitory factor), VIP (vasoactive intestinal peptide), GGF (glial growth factor), and IL-1 (interleukin-1). In related embodiments, the therapeutic agent is NGF or GNDF.

In embodiments, the therapeutic agent is a polypeptide, nucleic acid molecule, or fragment thereof that induces or enhances nerve growth. In related embodiments, the agent is an antibody, antibody fragment, or scFv that specifically binds to any of the neurotrophic agents described herein. In related embodiments, the agent is a nucleic acid molecule (e.g., DNA or RNA) that encodes any one of the neurotrophic agents described herein.

In embodiments, the therapeutic agent is a combination of any of the agents described herein.

Methods for evaluating a conduit comprising a therapeutic agent are well-known in the art. For example, the conduits of the in can be evaluated for the ability to release therapeutic agents using in vivo or in vitro methods. For example, a conduit of the invention may be allowed to incubate in a solution, e.g., an aqueous solution, for a prolonged period of time during which aliquots are removed and, tested for the amount of therapeutic agent released, and further, for the bioactivity of the agent. Alternatively, a conduit of the invention can be surgically implanted into an animal model (see, e.g., surgical animal models described below), and levels of the therapeutical agent can be monitored in, for example, the blood as a function of time.

The scaffolds of the invention can also deliver cellular substrates. Suitable cellular substrates include, but are not limited to, Schwann cells, oligodendrocytes, olfactory ensheathing glia (OEG), oligodendrocyte progenitor cells (OPC), embryonic stem cells (ESc), adult stem cells, induced pluripotent stem cells, differentiated ESc and differentiated adult stem cells, induced pluripotent stem cells (iPSc), and macrophages. Methods for delivering cellular substrates using a conduit of the invention are well-known in the art. For example, cellular substrates can be mixed within a gel, (e.g., Matrigel or fibrin gel) that would subsequently be used to fill the inside if a conduit before administration to a subject. See also Hurtado et al., *Biomaterials* 27:430-442 (2006); Chen et al., *Exp. Neurol.* 138:261-76 (1996); Takarai et al., *J. Neurosci.* 22:6670-81 (2002); Xu et al., *Exp. Neurol.* 134:261-72 (1995); and Xu et al., *J. Neurocytol.* 26:1-16 (1997), which are hereby incorporated by reference.

Methods of Treatment

The conduits of the present invention can be surgically implanted into a desired location in a subject by surgical procedures well-known in the art. For example, suitable surgical procedures am described in Hadlock et al., *Arch Otolaryngol. Head Neck Surg.* 124:1081 1086 (1998); WO 99/11181; U.S. Pat. No. 5,925,053; WO 88/06871; Wang et al., *Microsurgery* 14:608-618 (1993); and Mackinnon et al., *Plast. Reconst. Surg.* 85:419-424, (1990).

Figure 16:
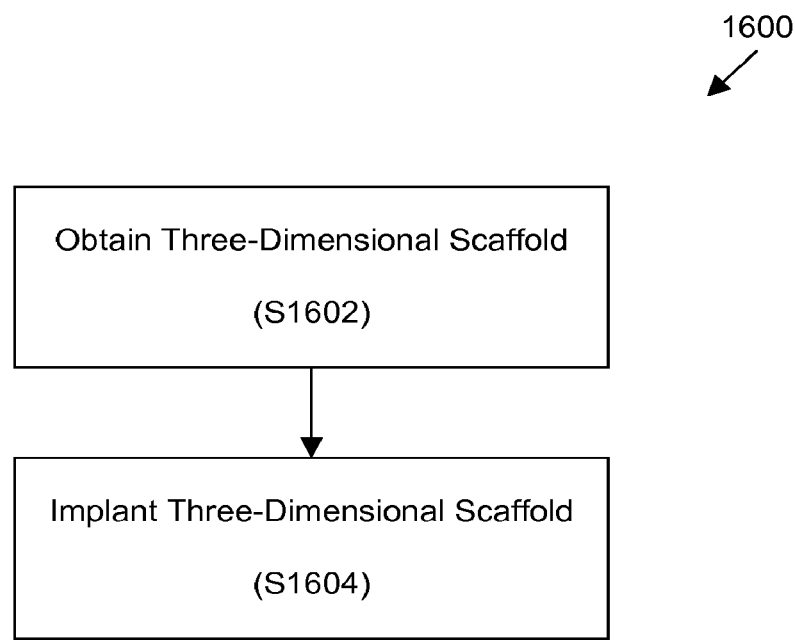
FIG. 16 depicts a method of treating a peripheral nerve or spinal cord injury in a mammalian subject according to an embodiment of the invention.

Referring now to FIG. 16, a method 1600 of treating a peripheral nerve or spinal cord injury is provided. Method 1600 is particularly useful in mammalian subjects.

In step S1602, a three-dimensional scaffold is provided. The three-dimensional scaffold can be a three-dimensional scaffold as described herein and can, for example, include at least one layer of highly-aligned fibers curved in a direction substantially perpendicular to a general direction of the fibers.

In step S1604, the three-dimensional scaffold is implanted at the site of the peripheral nerve or spinal cord injury to induce regeneration of the peripheral nerve or spinal cord.

EXAMPLES

It should be appreciated that the invention should not be construed to be limited to the examples that are now described; rather, the invention should be construed to include any and all applications provided herein and all equivalent variations within the skill of the ordinary artisan.

Example 1

Aligned Microfibers Foster Efficient Dorsal Root Ganglia Neurite Growth

Figure 3A:
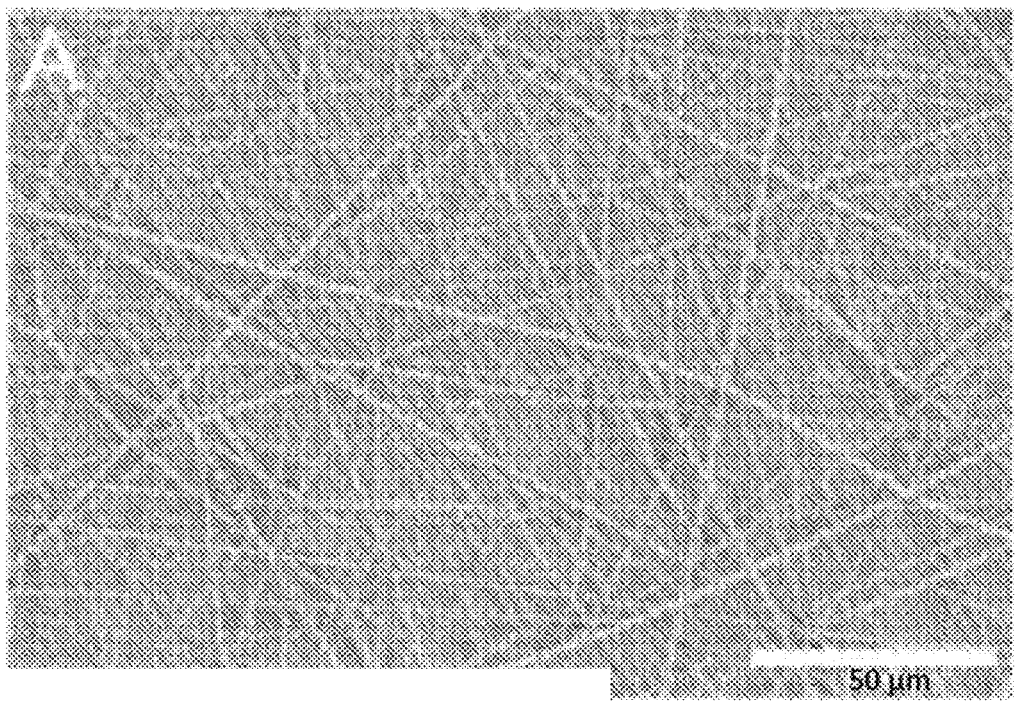
FIGS. 3A-3H show the results from scaffold characterization, and alignment quantification.
Figure 3B:
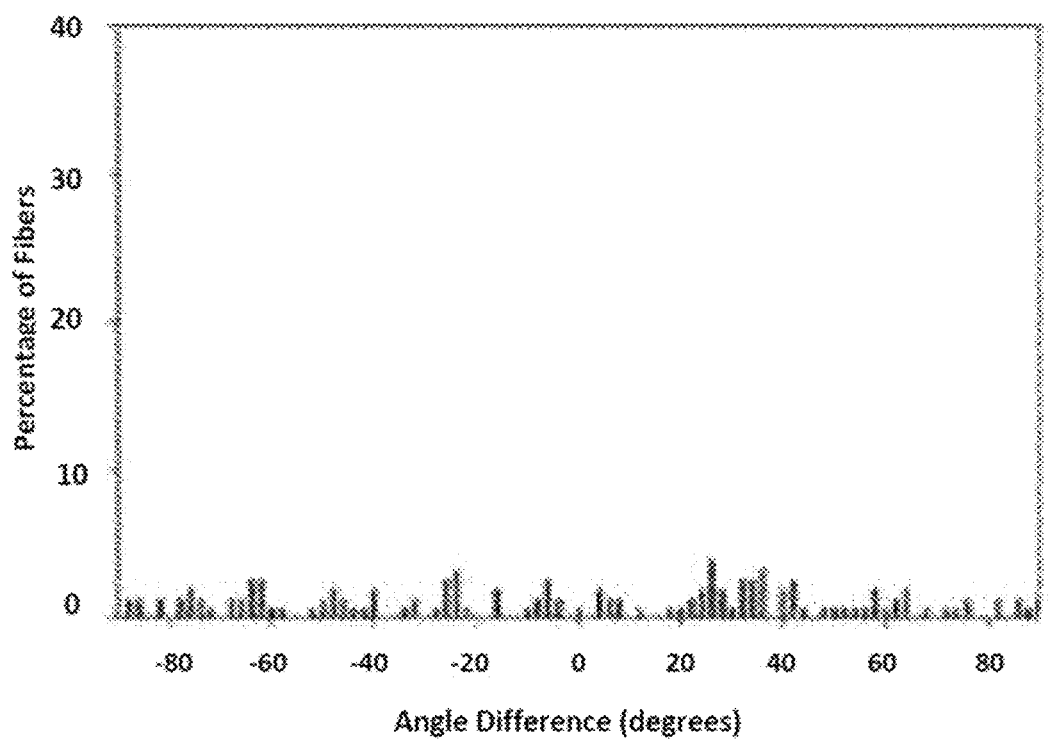
Figure 3C:
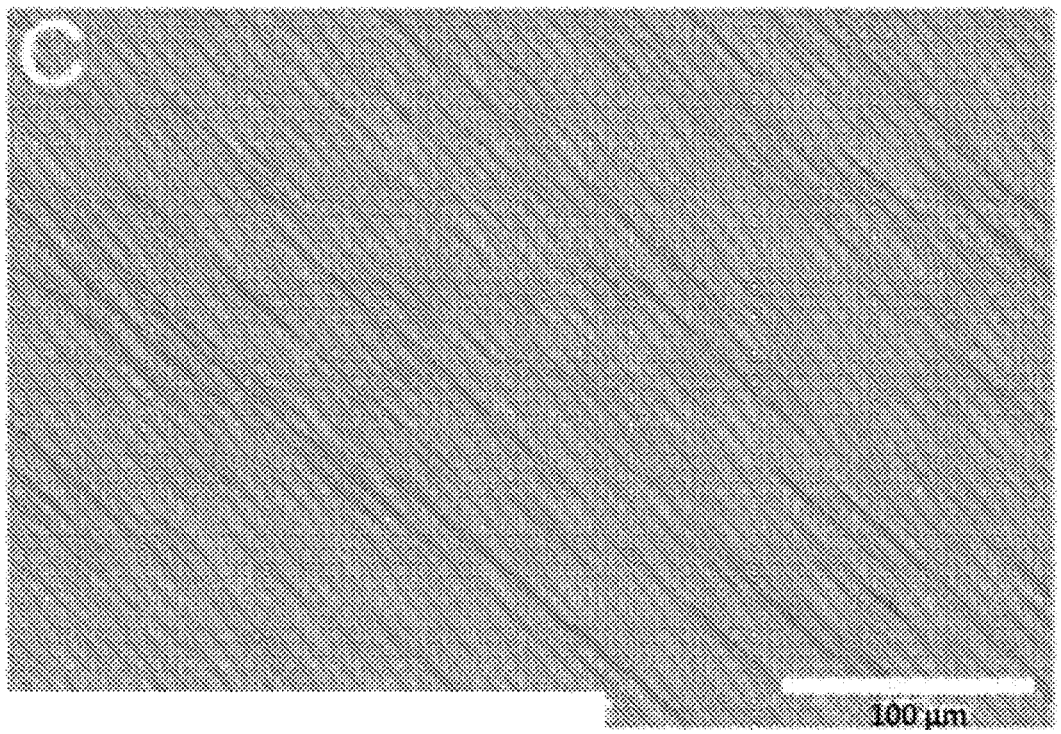
Figure 3D:
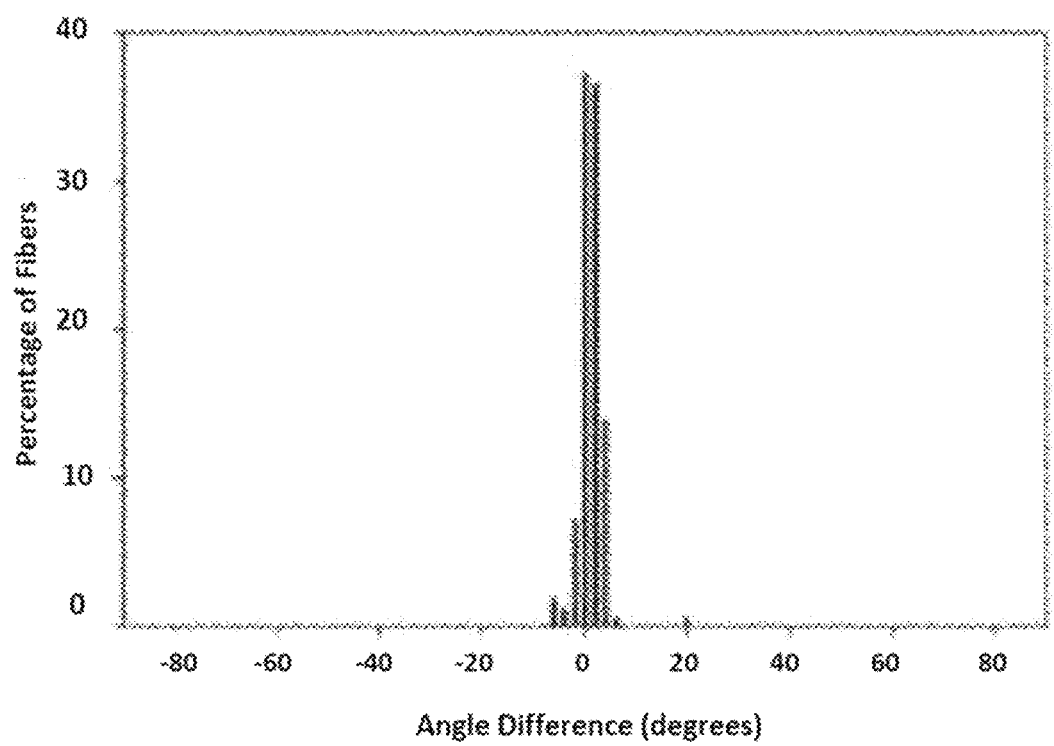
Figure 3E:
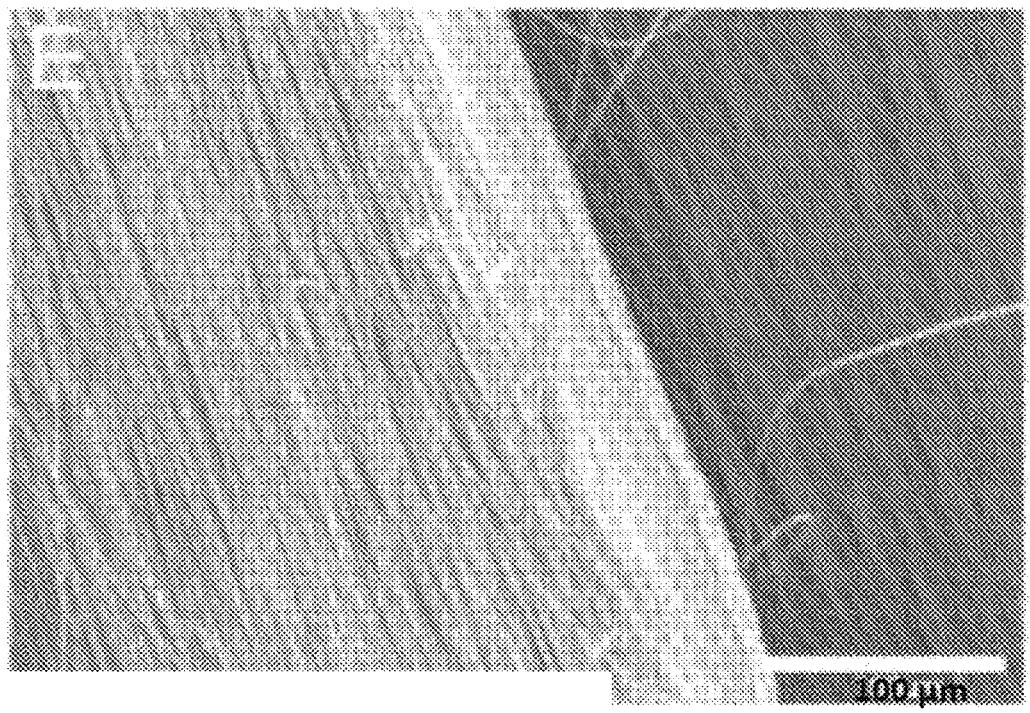

Polymer microfiber substrates were fabricated by electrospinning an 8% PLA solution onto 20 μm thin PLA films (FIG. 1) (Wang et al., 2009). Randomly oriented fibers were deposited on films by electrospinning PLA onto a stationary target; a rotating target was used to make aligned fiber substrates as described in our previous work (Wang et al., 2006). Fiber diameter and alignment were analyzed from scanning electron micrographs (FIGS. 2D and 2E and FIGS. 3A and 3C). Fiber diameter ranged between 1.2 and 1.6 μm. Only 4% of random fibers were found to fall within ±4° C. of the median fiber orientation (FIG. 3B), whereas 97.3% of aligned fibers fell within ±4° C. of the median orientation (FIG. 3D).

Figure 2A:
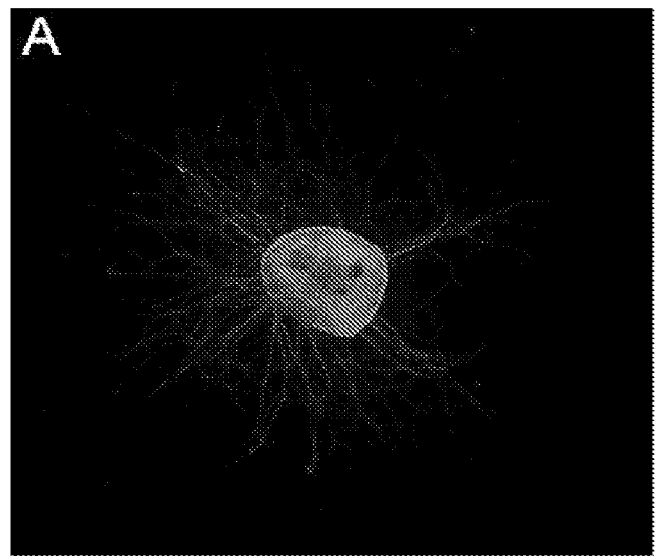
FIG. 2A-2H show how aligned polymer fibers specify the direction of DRG neurite growth.
Figure 2B:
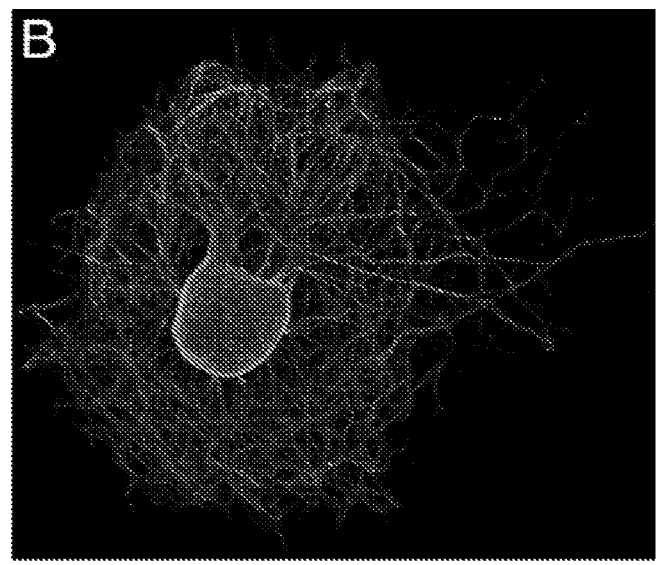
Figure 2C:
Figure 2D:
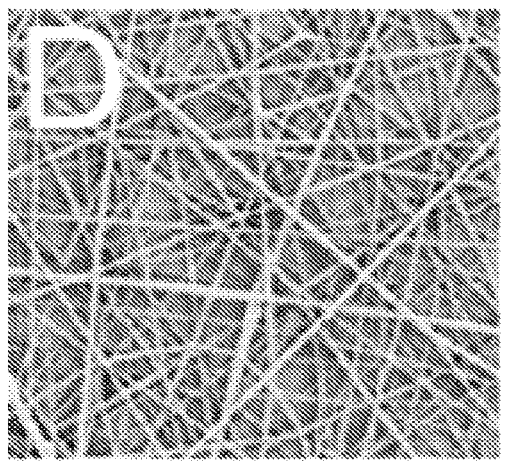
Figure 2E:
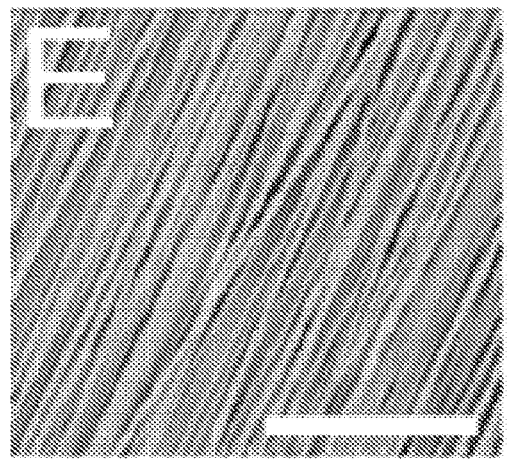
Figure 2F:
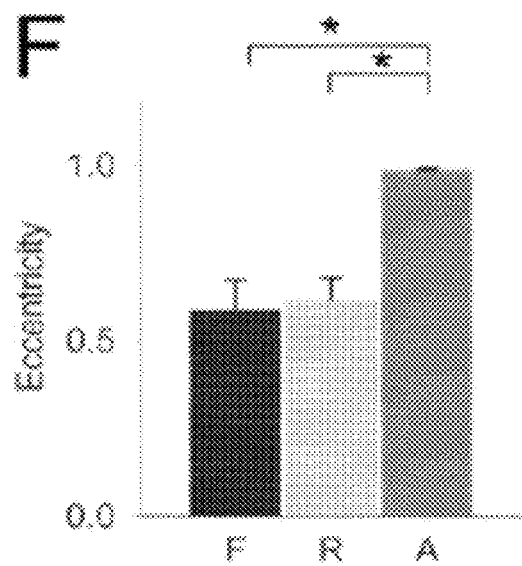
Figure 2G:
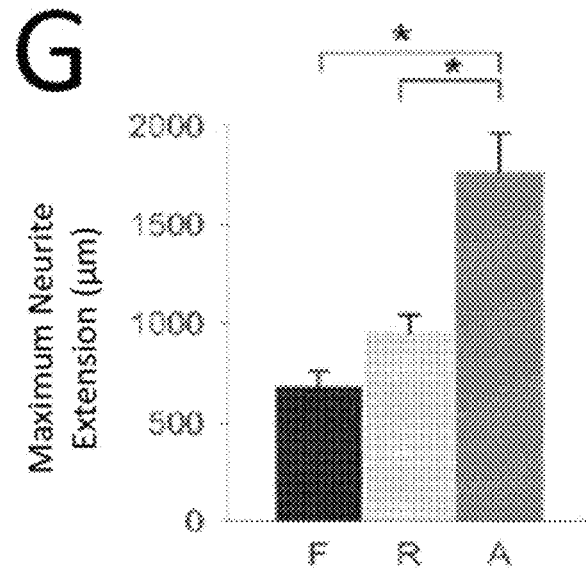
Figure 2H:
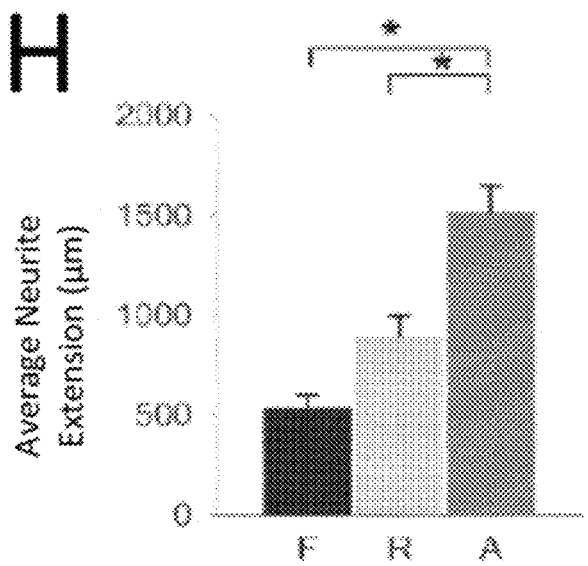

Dorsal root ganglia (DRG) isolated from P4 rat pups were cultured on film, random, and aligned fiber substrates for 5 days in serum free media (n=6). DRG cultured on film and random fiber substrates projected neurites without preferential direction (FIGS. 2A and 2B). However, in the presence of aligned PLA fibers, DRG projected linear neurites following the polymer microfiber orientation (FIG. 2C), Explants cultured on aligned PLA microfibers demonstrated a significant increase in eccentricity, a measure of anisotropy (FIG. 2F). Neurites from DRG cultured on aligned fibers readied significantly greater maximum and average distances compared with random fiber and film controls (P<0.05) (FIGS. 2G and 2H). Next, it was determined whether topography alone (regardless of orientation) can induce a differential response from DRG neurons. Neurites of DRG cultured on random fibers were more dense (FIGS. 2A and 2B); however, the average and maximum distance readied by neurites was similar to that of DRG cultured on film substrates (FIGS. 2G and 2H). Increases in maximum and average neurite distance on aligned fibers (FIGS. 2G and 2H) are likely due to increased growth efficiency when neurites align with the underlying topography.

Example 2

Microtopography Supports Host Tissue Integration and Gap Closure

Figure 3F:
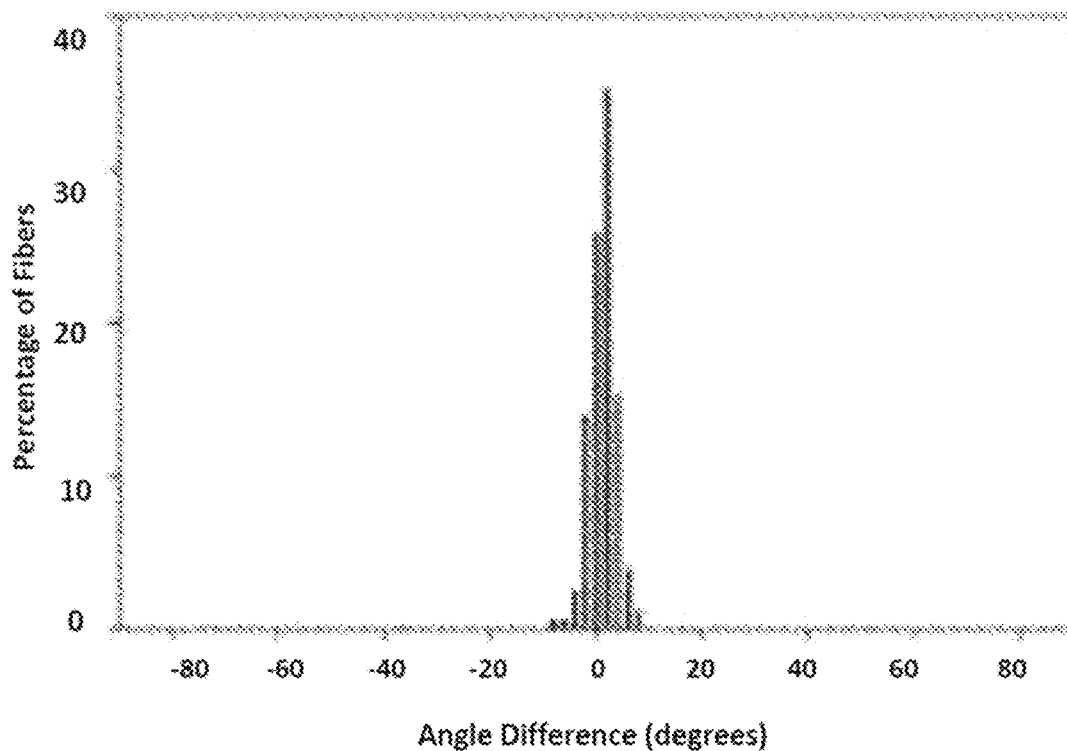
Figure 3G:
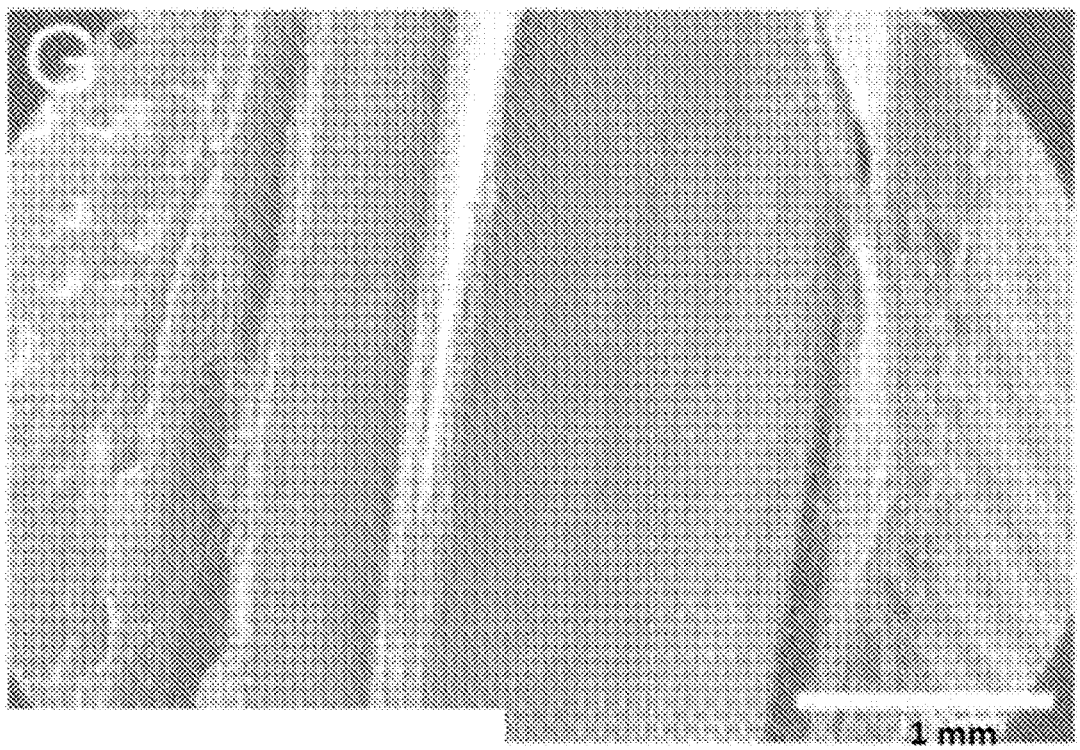
Figure 3H:
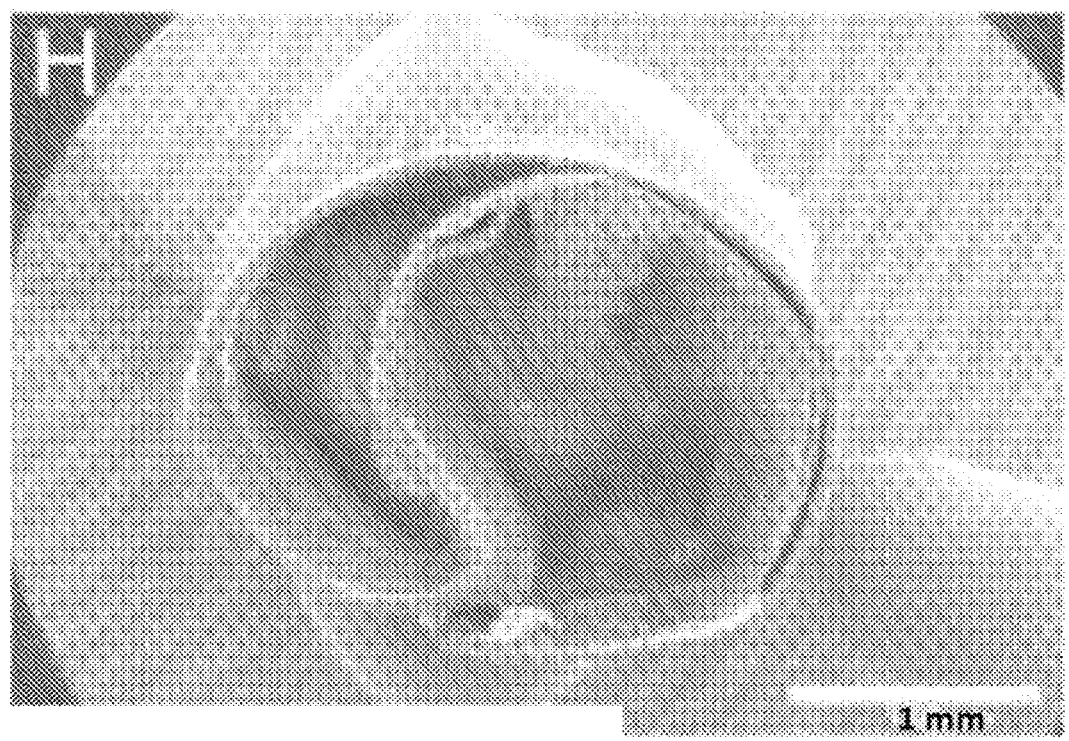
Figures 13A, 13B, 13C, 13D, 13E, 13F:
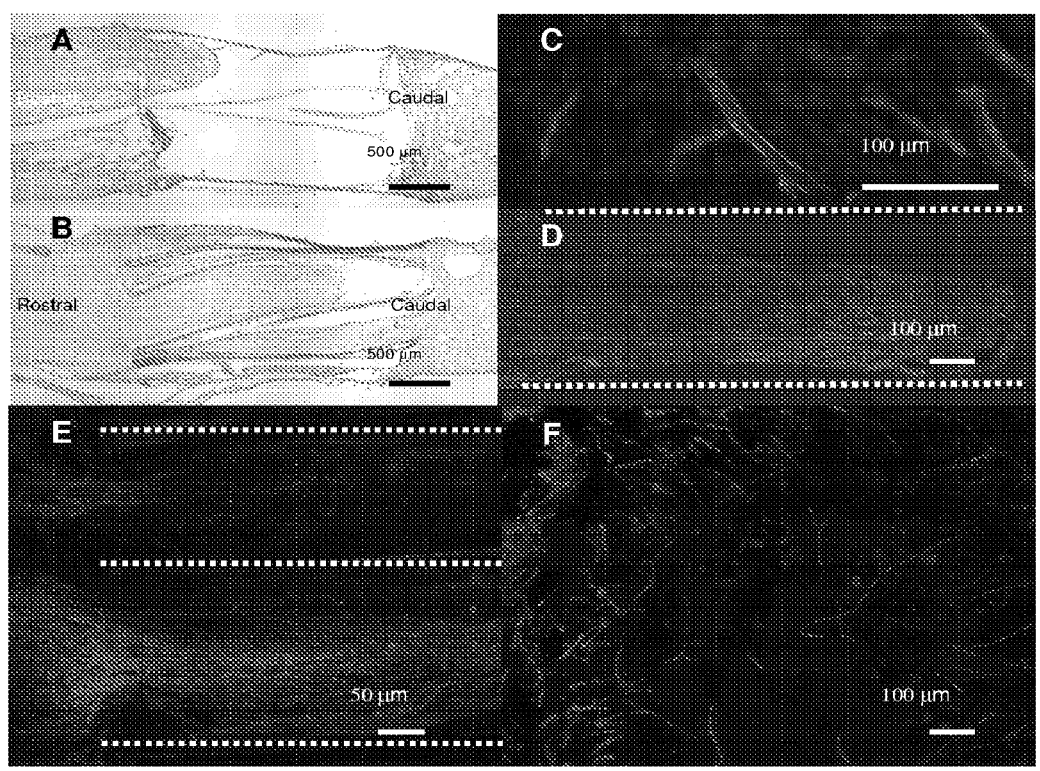
FIGS. 13A-13F show the transplantation results in a complete transection rat spinal cord injury model.
Figure 14A:
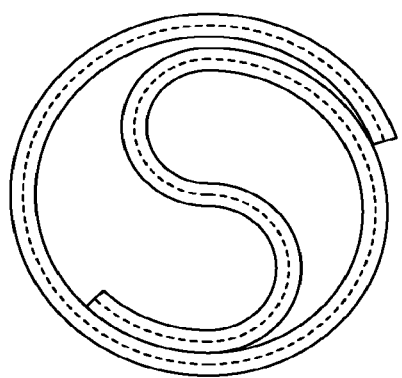
FIGS. 14A-14H depicts various geometries of three-dimensional scaffolds according to embodiments of the invention.
Figure 14B:
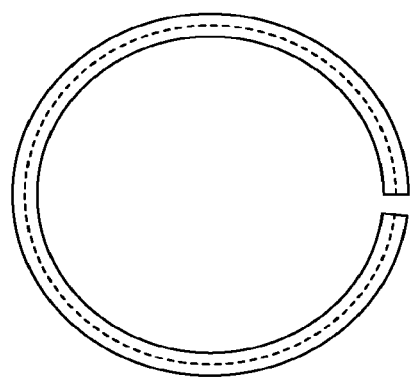
Figure 14C:
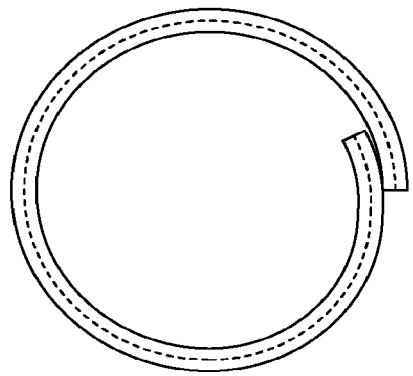
Figure 14D:
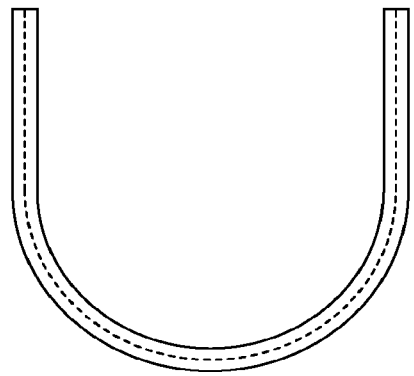
Figure 14E:
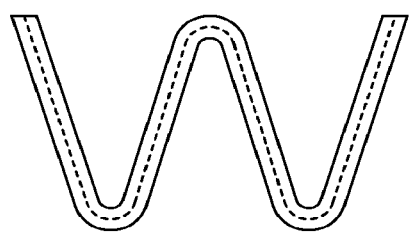
Figure 14F:
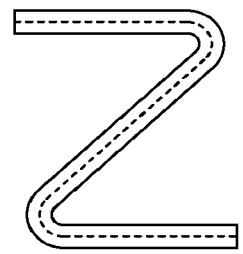
Figure 14G:
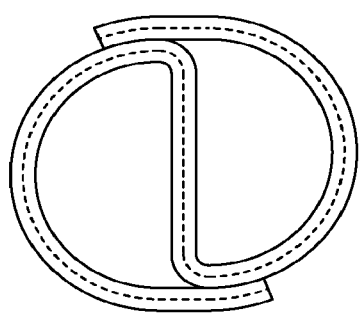
Figure 14H:
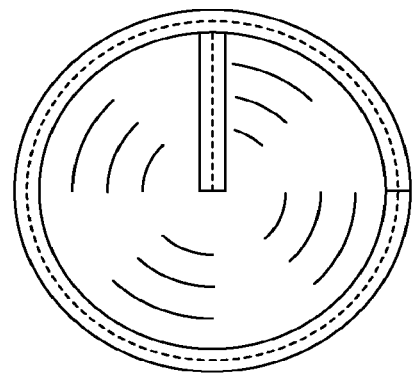

Guidance conduits were fabricated from film, random and aligned fiber 2D substrates rolled into conduits (FIGS. 1C-1F and FIG. 3H). Importantly, conduit fabrication did not perturb fiber alignment. 93.3% of fibers fell within ±4° C. of the median orientation post-fabrication (FIG. 3F). An unambiguous, complete transection model of rat spinal cord injury was used to test the hypothesis that aligned microfibers promote axonal regeneration after CNS injury (FIG. 13). A 3 mm gap was created in the spinal cord (thoracic 9) of adult rats, and immediately after, film, random, or aligned fiber conduits filled with a fibrin gel were grafted into the gap (FIG. 4). Animals from each group were perfused 1 (n=3), 2 (n=3), and 4 weeks (n=7) following injury/implantation. The results, from the 4 week time point were gathered in two independent experiments of n=3 and n=4 for each group.

Figures 5A, 5B, 5C, 5D, 5E, 5F, 5G, 5H, 5I, 5J, 5K, 5L:
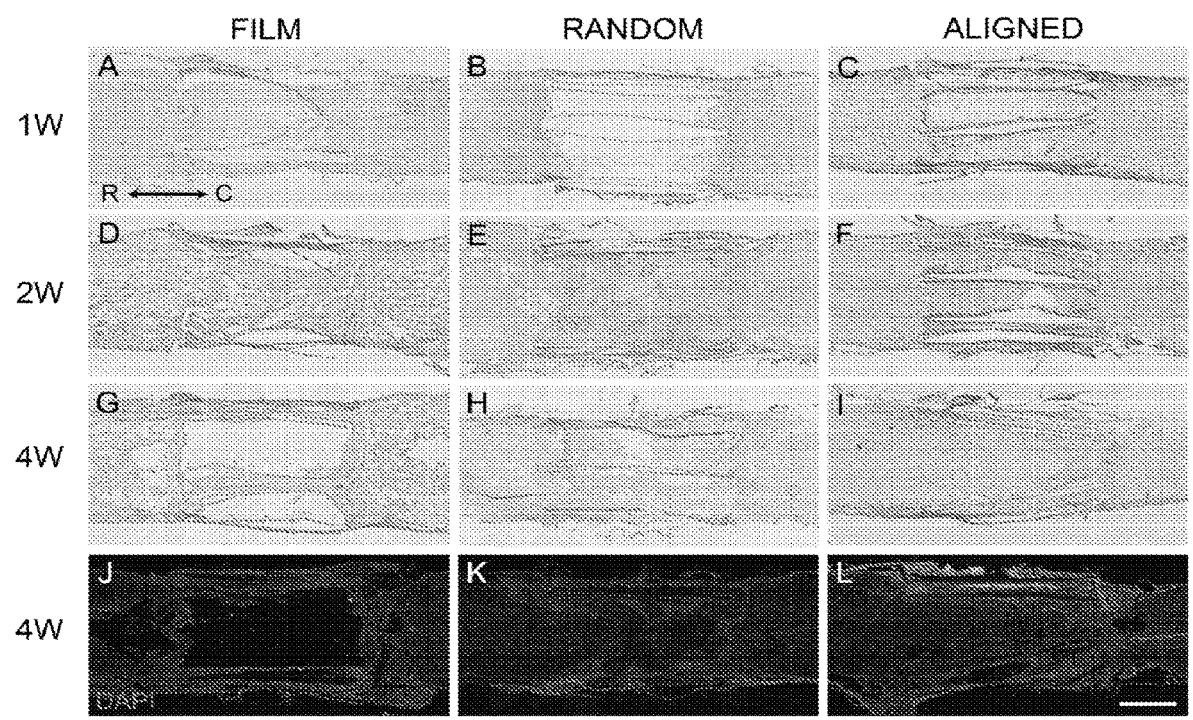
Figure 6A:
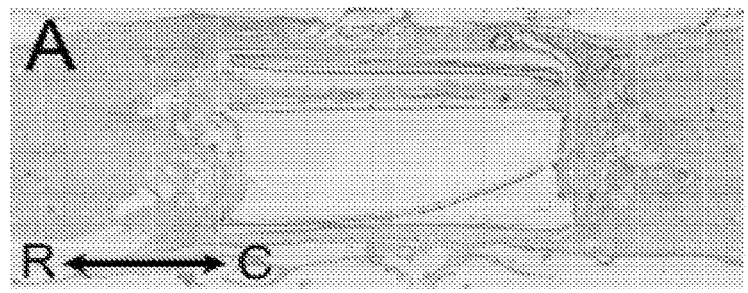
FIGS. 6A-6D show that microtopography promotes host tissue integration and gap closure. 3 mm long conduit was implanted to bridge a complete transection spinal cord injury (see FIG. 4). Cresyl violet was used to visualize tissue architecture.
Figure 6B:
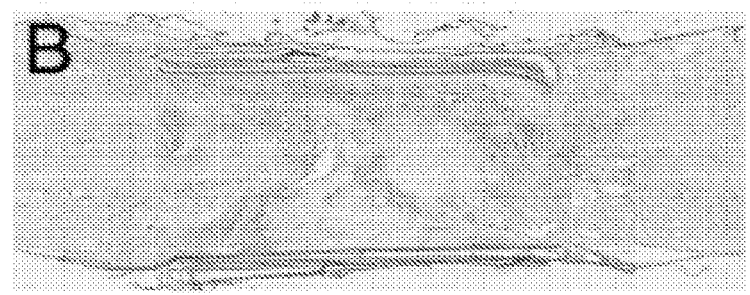
Figure 6C:
Figure 6D:
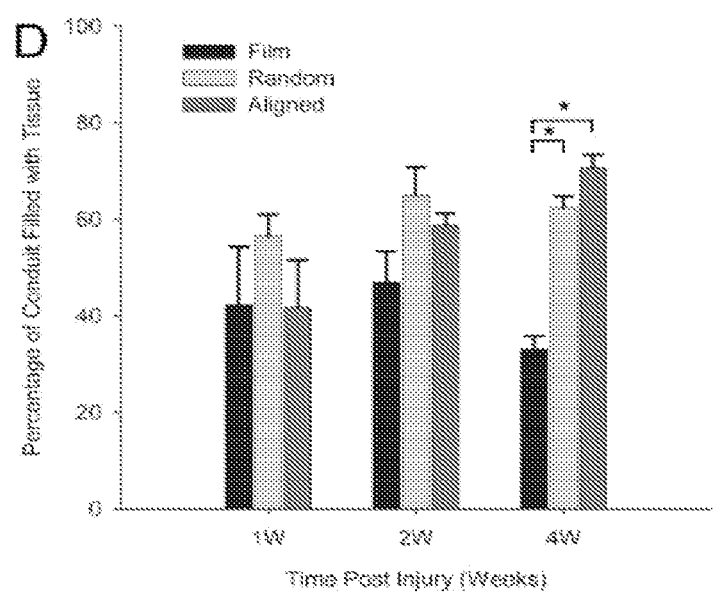

Cresyl violet and DAPI staining were used to assess cytoarchitecture in horizontal spinal cord sections. One week after transplantation remnants of the fibrin gel were present inside conduits and host cells had infiltrated the conduits' lumen (FIGS. 5A-5C). Cell population increased substantially by two weeks in all groups (FIGS. 5D-5F); however, at this time point film conduits started to show a decrease in transverse diameter of the lumen content (FIG. 5D). By 4 weeks, film conduits presented thin tissue strands and large (>1 mm diameter) cavities had developed at the rostral (2/7 animals) and caudal (4/7 animals) graft-cord interfaces (FIG. 6A and FIGS. 5G-5L). In contrast, conduits with random or aligned microfibers promoted tissue sparing at both interfaces, where 1 out of 14 animals with either random or aligned fiber conduits had a cavity in the caudal spinal cord at 4 weeks. Additionally, random and aligned fiber conduits were filled with host tissue at 4 weeks after implantation and the initial 3 mm tissue gaps were closed by endogenous cell populations (FIGS. 6B and 6C; and FIGS. 5H, 5I, 5K, and 5L). One remarkable observation was the tissue continuity at the rostral interface of random and aligned fiber conduits (FIGS. 6B and 6C; and FIGS. 5H and 5I). In contrast, a scar-like matrix developed at both interfaces of film conduits, and exclusively at the caudal interface of random and aligned fiber conduits (FIGS. 6B and 6C; and FIGS. 5H and 5I). A Cavalieri estimator probe was used to quantify the percentage of conduit volume filled with tissue. Both random and aligned fiber conduits had significantly more host tissue than film conduits at 4 weeks (P<0.05). No significant differences were observed at 1 or 2 weeks following implantation (FIG. 6D).

Figure 7A:
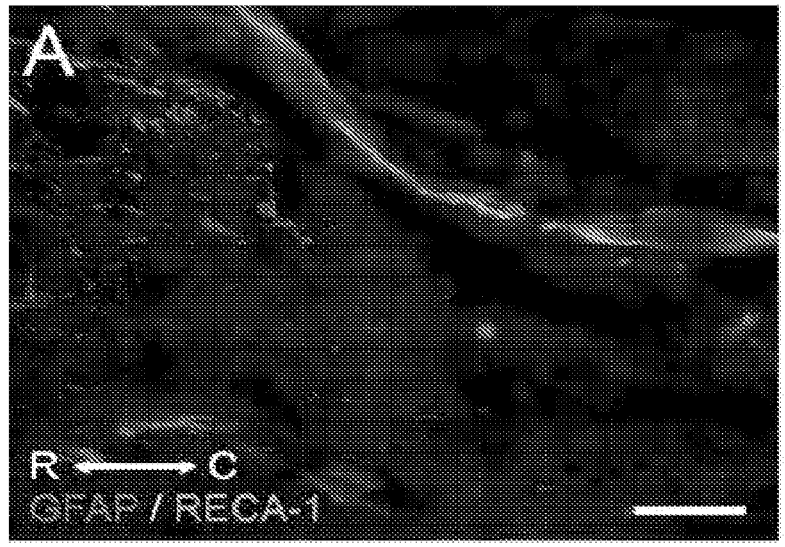
FIGS. 7A -7C include immunostaining images showing that grafts support angiogenesis and are well vascularized 4 weeks following conduit implantation. Blood vessels are observed, by immunostaining for rat endothelial cell antigen 1, at the rostral cord interface 1 week after implantation (FIG. 7A)., and in the center of the graft at 4 weeks (FIG. 7B).
Figure 7B:
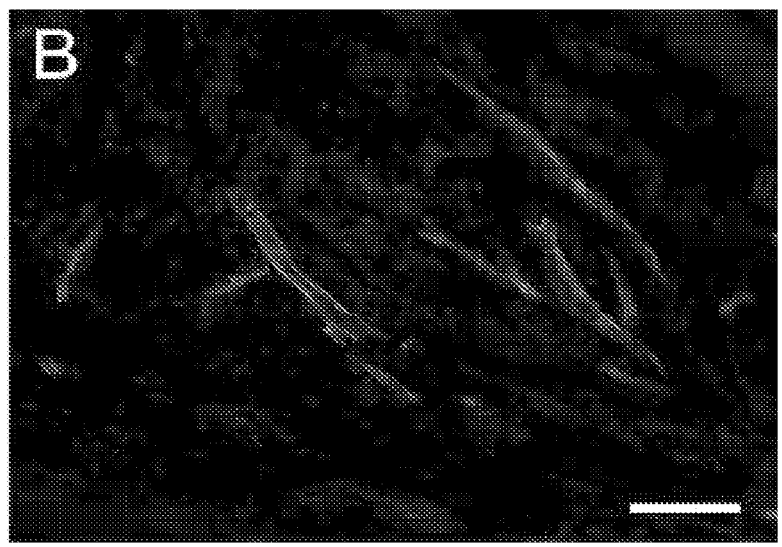
Figure 7C:
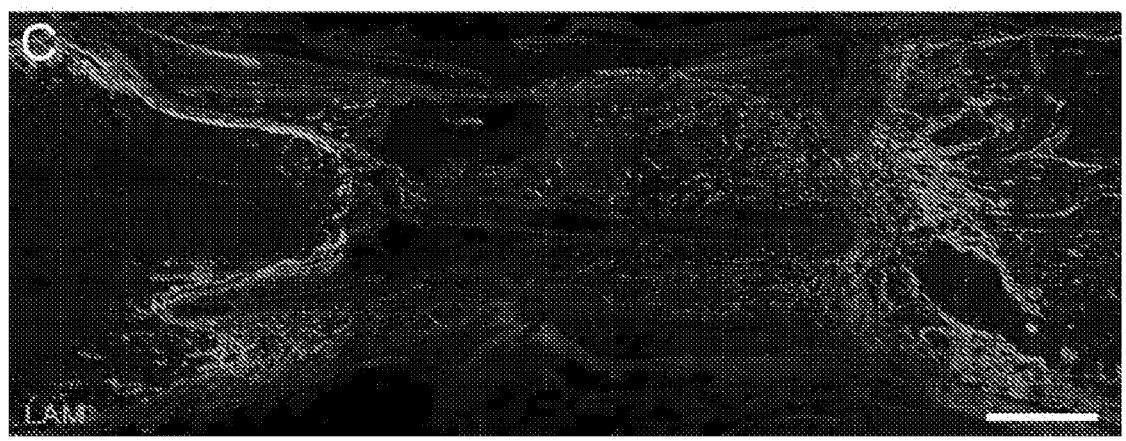

In a third independent experiment, the site of injury was re-exposed at 4 weeks in six animals that received aligned fiber grafts. Upon re-exposure, it was noted that the grafts retained their original placement and maintained good apposition to the rostral and caudal spinal cord stumps. Opening the grafts by a midline longitudinal incision on the dorsal surface revealed a large diameter tissue cable containing thin and dispersed blood vessels that had formed between the rostral and caudal stumps, Staining of horizontal cryostat sections for rat endothelial cell antigen (RECA-1) demonstrated the presence of blood vessels at the immediate graft-cord interface at 1 week (FIG. 7A) and up to the center of the graft at 4 weeks (FIG. 7B). Laminin staining for basement membrane showed extensive vasculature at both the rostral and caudal spinal cord 4 weeks after injury, although the distribution of blood vessels differed between stamps. The rostral stump contained parallel arrays of longitudinally aligned blood vessels, and although the caudal stump appeared more vascularized, blood vessels were disorganized (FIG. 7C).

Example 3

Aligned Fibers Promote Robust, Long Distance Axonal Regeneration

Figures 8A, 8B, 8C, 8D, 8E, 8F, 8G, 8H, 8I:
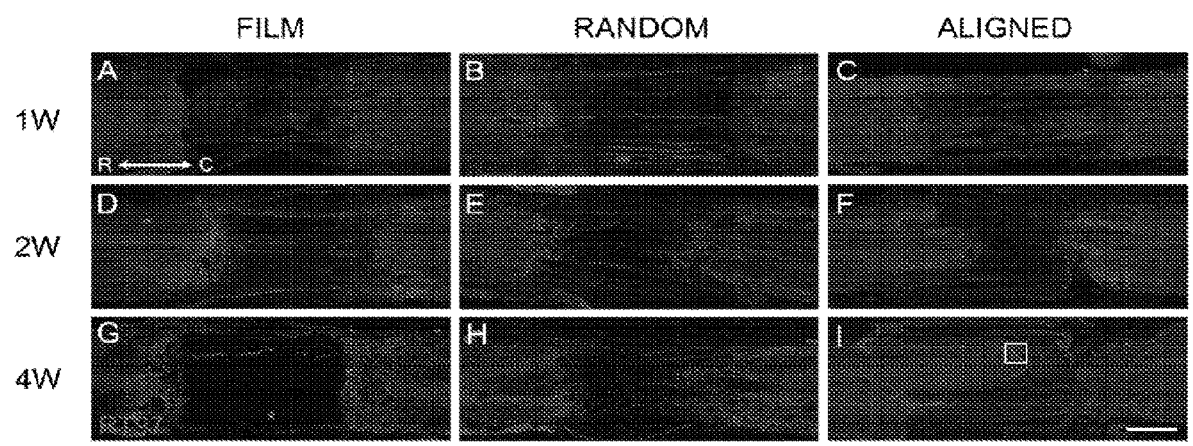
FIGS. 8A-8M show that aligned fibers promote extensive axonal regeneration, immunostaining to neurofilament (RT97) was used to visualize axons.
Figure 8J:
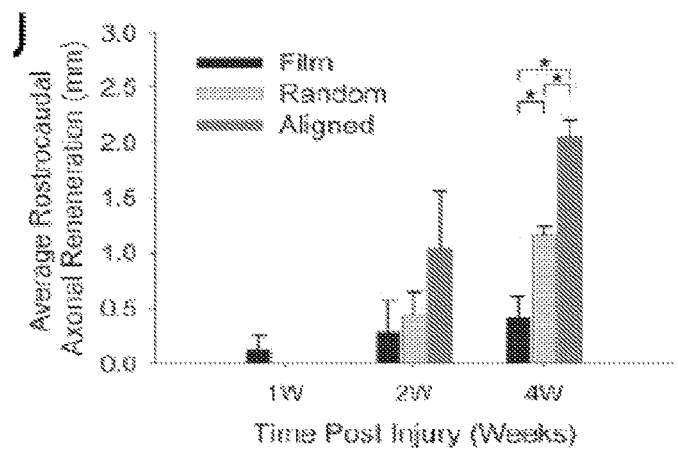
Figure 8K:
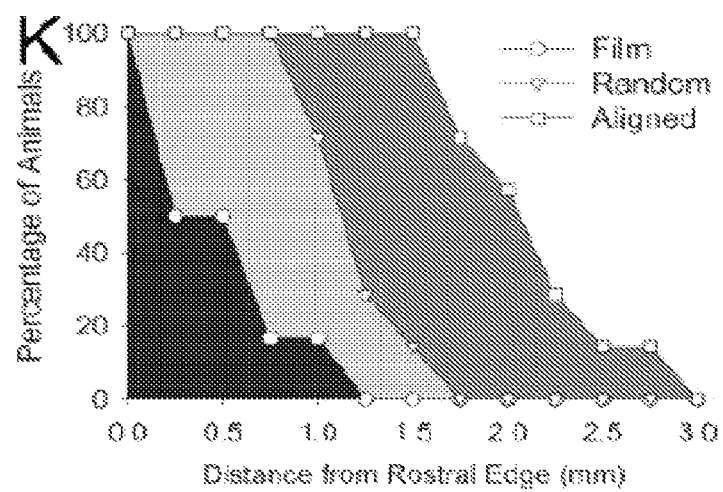
Figure 8L:
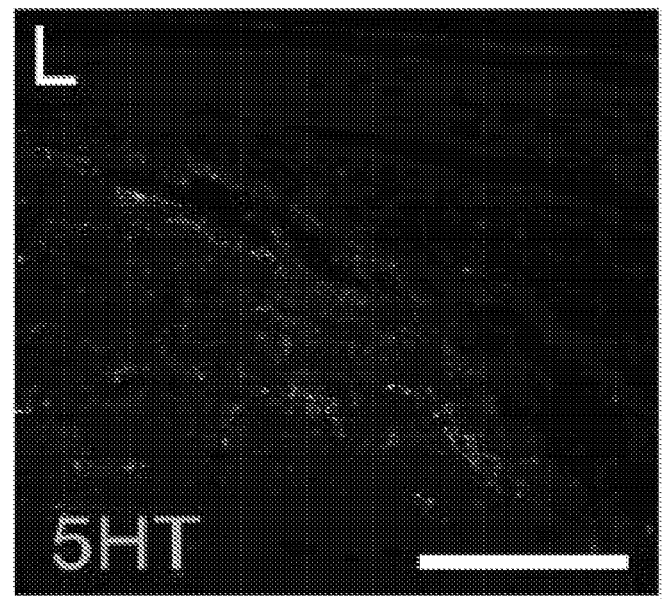

Horizontal sections were immunolabeled for neurofilament (RT97) and serotonin (5HT) to examine axonal regenerating after complete spinal cord transection. Neurofilament section overviews demonstrated robust rostrocaudal axonal regeneration into aligned fiber conduits. One week after implantation, all groups displayed a similar pattern of RT97 staining (FIGS. 8A-8C). However, by 2 weeks neurofilament staining demonstrated robust rostrocaudal growth into aligned fiber conduits (FIG. 8F) that further elongated by 4 weeks (FIG. 8I). This response was observed exclusively from the rostral spinal cord. In random fiber conduits, individual RT97$^+$ axons entered the grafts at 2 weeks (FIG. 8E), and a modest rostrocaudal response was observed by 4 weeks (FIG. 8H). In film conduits, very few axons were present at the interface at 2 weeks (FIG. 8D), and at 4 weeks sparse RT97$^+$ axons were seen inside thin tissue strands (FIG. 8G). Axonal regeneration was quantified by measuring the distance between the rostral edge of the conduit to the 'axonal front', defined as the point of 10 or more contiguous axons (Shen et al., *Science* 326:592-6 (2009)). Markedly, over 4 weeks, aligned fiber conduits promoted long distance axonal regeneration (2055±150 µm), significantly greater than random fiber (1162±87 µm) and film (413±199 µm) conduits (FIG. 8J). At 4 weeks, all 7 animals from the aligned fiber group had robust regeneration present 1.5 mm from the rostral edge of the conduit compared with 1 animal from the random and 0 from the film groups (FIG. 8K). A considerable number of raphespinal (5HT$^+$) axons were identified within the regeneration response (FIG. 8L). Retrograde tracing was used to identify neurons that regenerated axons inside conduits in 6 additional rats that received aligned fiber grafts. Fast blue was injected in the center of the tissue cable present inside the graft 4 weeks after implantation. Fast blue positive neurons were identified in the spinal cord rostral to the conduit as well as in the raphe nuclei (64.5±54.7), reticular formation (175.5±105.9), red nucleus (68±83), and the vestibular nuclei (28.5±26.5).

Figure 8M:
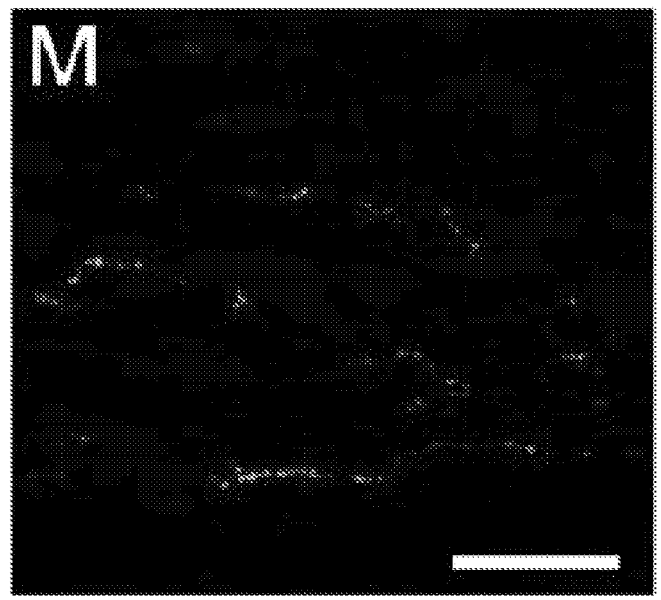
Figure 9:
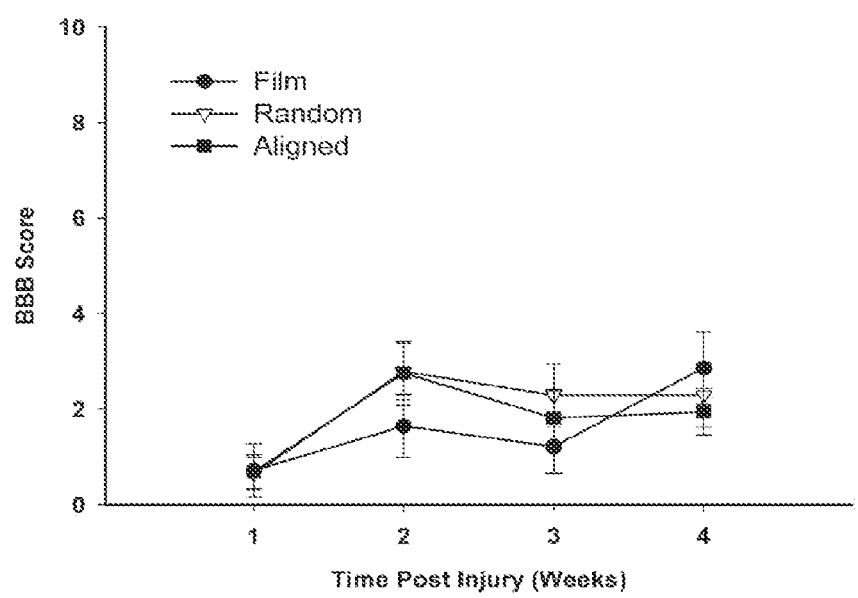
FIG. 9 includes a graph showing changes in hindlimb function. Changes in hindlimb function were assessed using the Basso, Beattie, and Bresnahan (BBB) open field test for locomotor recovery. No significance was observed for differences between groups at 1, 2, 3 or 4 weeks by repeated measures ANOVA.

At 4 weeks. 5HT$^+$ axons were present approximately 1 mm caudal to the graft in 3/21 animals (2 random, 1 aligned fiber) (FIG. 8M). It is important to note that 5HT fibers undergo Wallerian degeneration after complete transection spinal cord injury, and by day 14 only a few fibers (<1%) remain scattered chiefly in the lumbar cord. These observations are consistent with the findings of Cheng and Olson, *Exp. Neurol.* 136:149-61 (1995), in that a few aberrant, residual 5HT$^+$ fibers are present in the lumbar cord at 2 weeks following injury, Cheng et al. (1995) also reported that at 21 days after injury almost all 5HT$^+$ fibers in the caudal cord have disappeared and no fibers can be found 30 days after complete transection injury. Therefore, the presence of serotonergic fibers below the level of the injury is indicative of axonal regeneration beyond conduits. Despite the presence of serotonergic axons caudal to the graft in 3/21 animals, no differences were detected in hindlimb function using the scale developed by Basso, Beattie, and Bresnahan (FIG. 9) (Basso et al., *J. Neurotrauma* 12:1-21 (1995); and Basso et al., *Exp. Neurol.* 139:244-56(1996)).

Example 4

Astrocytes Support Regenerating Axons

Figures 10A, 10B, 10C, 10D, 10E, 10F, 10G, 10H, 10I:
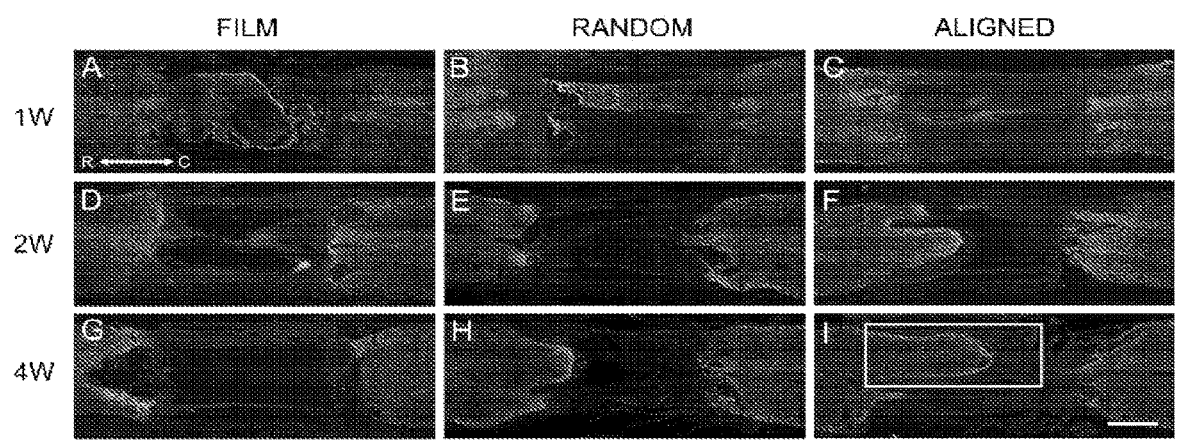
FIGS. 10A-10L show that axonal regeneration is localized to migratory astrocytes. GFAP staining was used to visualize astrocytes.
Figure 10J:
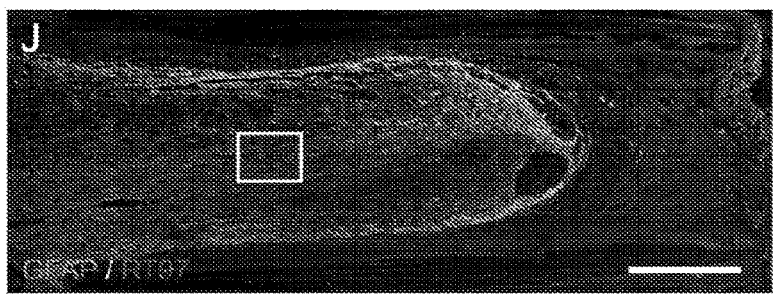
Figure 10K:
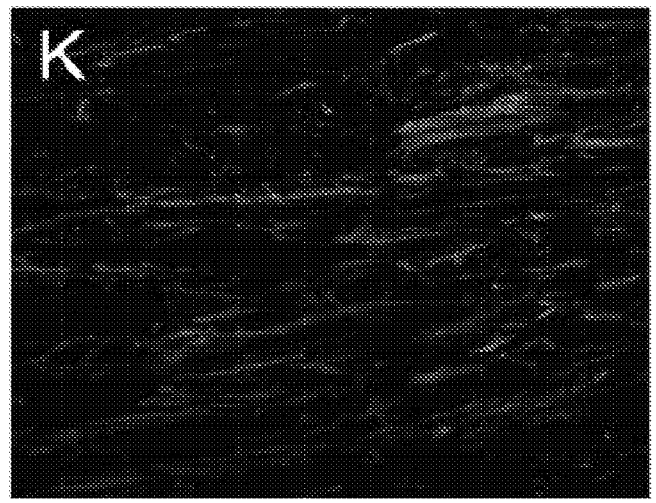
Figure 10L:
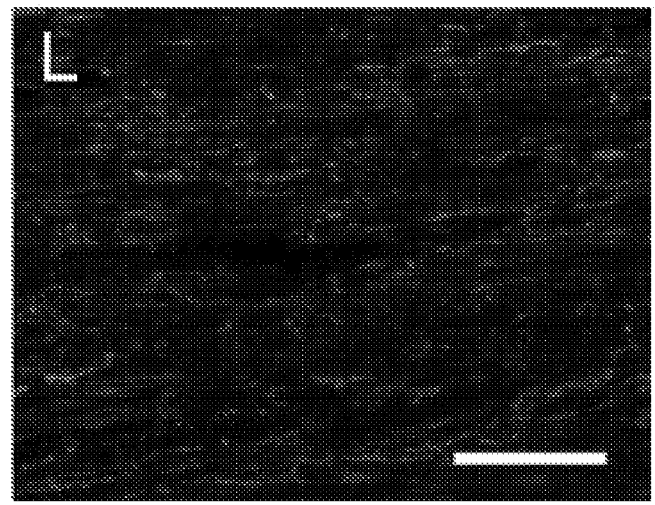
Figure 11A:
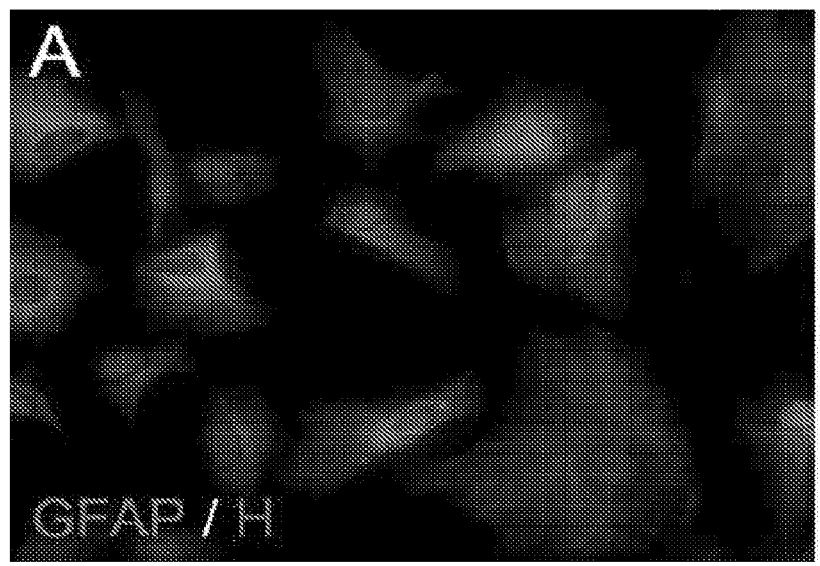
FIGS. 11A-11C include cell staining images showing that astrocytes exhibit morphological sensitivity to topographic cues. Astrocytes isolated from neonatal rat cortices were cultured for 48 hours on film (FIG. 11A), random (FIG. 11B), and aligned fiber (FIG. 11C) substrates. Arrows indicate close apposition of astrocytes to underlying polymer fibers in FIG. 1B. (Scale bar, 100 µm).
Figure 11B:
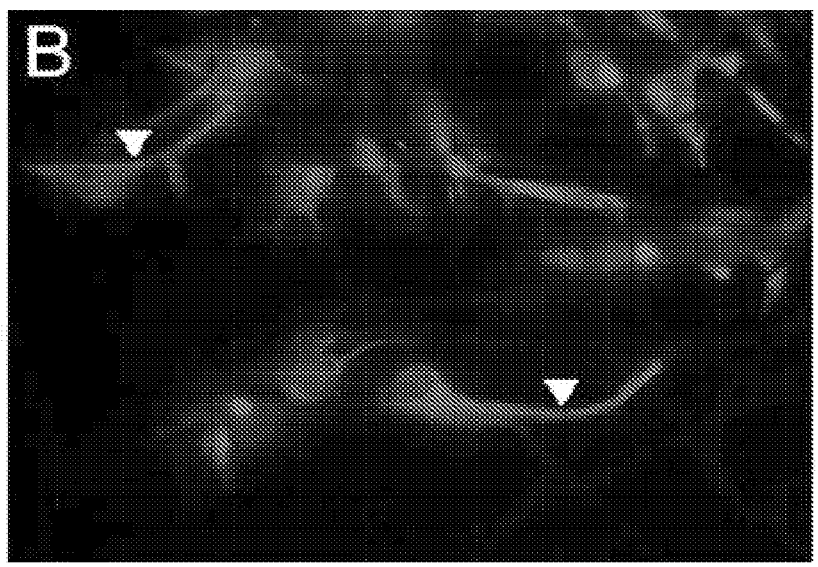
Figure 11C:
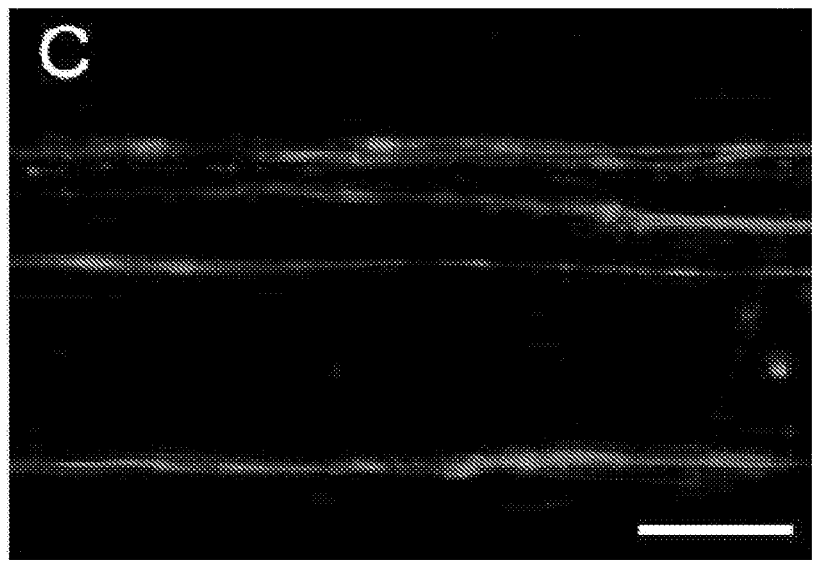

Areas void of astrocytes were observed at the rostral cord in animals that received film conduits (FIGS. 10A, 10D, and 10G). Conversely, migration of astrocytes was observed in the rostrocaudal direction for random and aligned fiber conduits to an extent similar to the axonal growth (FIGS. 10B, 10C, 10E, 10F, 10H, and 10I). In the caudal stump, areas void of astrocytes were observed in all animals (FIGS. 10A-I). Double-labeling for GFAP and RT97 indicated (hat the robust axonal regeneration response observed in aligned fiber conduits occurred in close proximity with astrocytes (FIG. 10J). High-resolution confocal imaging showed morphologically aligned astrocytes in close proximity to regenerating axons in aligned fiber conduits (FIGS. 10K and 10L). It was then determined whether astrocytes cultured on aligned PLA fibers respond to the underlying topography. Interestingly, astrocytes exhibited a linear morphology when cultured on aligned fibers (FIG. 11C).

Figure 12A:
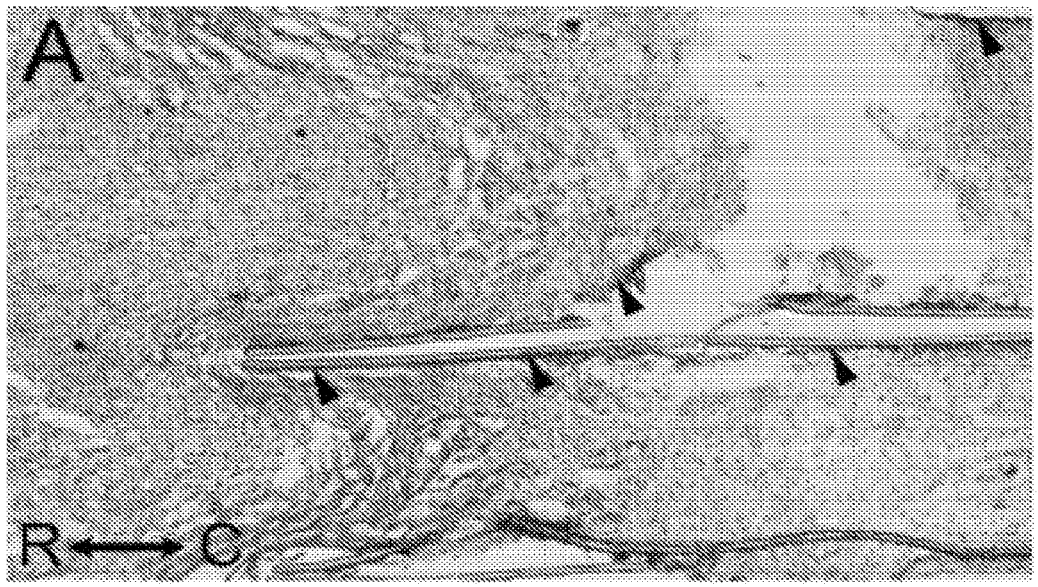
FIGS. 12A-12D include tissue staining images showing how pioneer axons guide the regeneration response from the rostral spinal cord.
Figure 12B:
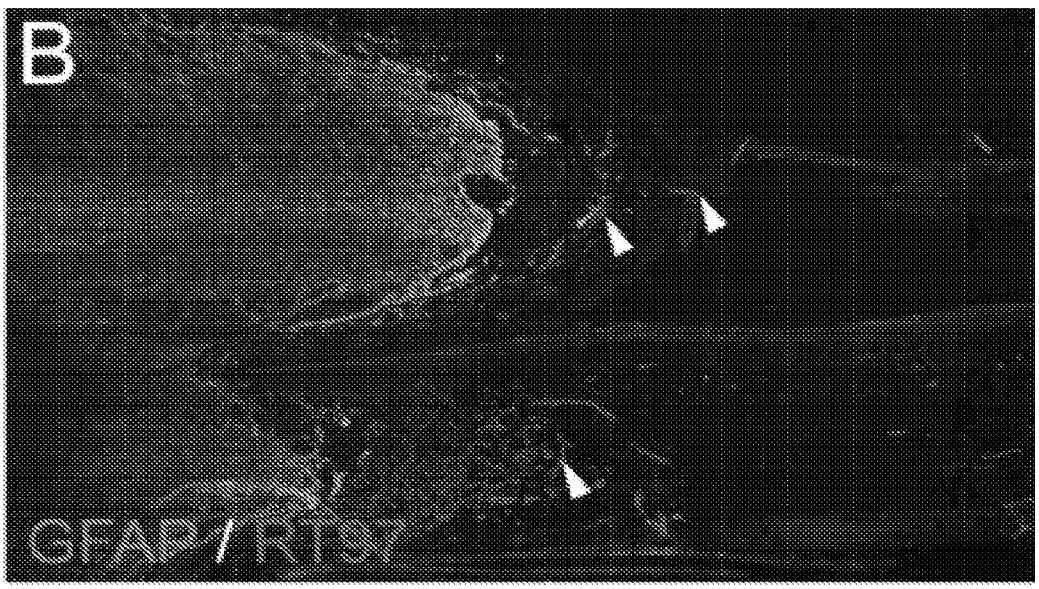
Figure 12C:
Figure 12D:
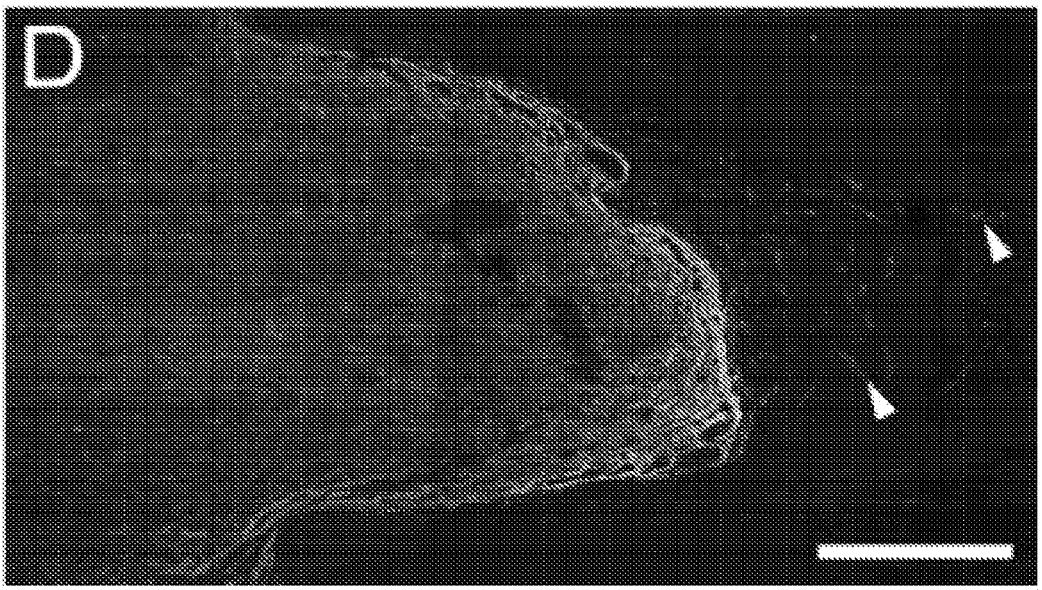

In order to assess the contribution of astrocytes to the axonal regeneration response, it was important to determine one of three alternatives: (1) astrocytes migrate into the conduit ahead of axons; (2) axons regenerate ahead of astrocytes: or (3) astrocytes and axons travel together. By examining the regeneration front in sections labeled for GFAP and RT97, a number of leading pioneer axons were observed in front of the bulk response at 4 weeks (FIGS. 12B and 12D). This observation was pervasive in all animals with a robust response from the rostral spinal cord. In adjacent cresyl violet sections, bright field microscopy revealed the presence of polymer fibers that detached from the wall of random (FIG. 12A) and aligned fiber (FIG. 12C) conduits. These fibers were located ahead of the bulk tissue response matching the distribution of pioneer axons.

Spontaneous axonal regeneration after spinal cord injury is limited (Silver and Miller, *Nat. Rev. Neurosci.* 5:146-56 (2004); and Ylera et al., *Curr. Biol.* 19:930-6 (2009)). Traditional repair strategies have been successful in eliciting long distance regeneration of isolated axons. These approaches generally incorporate one or more components used to enhance regeneration, including potent promoters of neurite growth (NGF, NT-3, GDNF, BDNF, laminin) and growth permissive cells (i.e., Schwann cells, olfactory ensheathing glia) (Berry et al., Brain Res Bull 20:223-31 (1988a); Berry et al., *J. Neurocytol*, 17:727-44 (1988b); Coumans et al., *J Neurosci.* 21:9334-4 (2001); David and Aguayo, *Science* 214:931-3 (1981); Houle et al. *J. Neurosci.* 26:7405-15 (2006); Hurtado et al., *Biomaterials* 27:430-42 (2006); Oudega and Hagg, *Exp. Neurol.* 140:218-29 (1996); Pearse, et al., *Nat. Med.* 10:610-6 (2004); Richardson et al., *Nature* 284:264-5 (1980); Stokols and Tuszynski, *Biomaterials* 27:443-51 (2006); Tom et al., *J. Neurosci.* 29:14881-90 (2009); Tuszynski and Gage, *Proc. Natl. Acad. Sci. USA* 92:4621-5 (1995); Xu et al., *Exp. Neurol.* 134:261-72 (1995a); and Xu et al., *J. Comp. Neurol.* 351:145-60 (1995b)). As discussed in detail above, it has now been discovered that an aligned microfiber-based synthetic polymer substratum is capable of promoting robust CNS tissue. growth without neurotrophin administration or cell transplants. Use of the aligned microfiber-based synthetic polymer substratum results in a long distance (2055±150 µm) of axonal regeneration, which is supported by migrating astrocytes. This response is remarkably similar to successful modes of PNS regeneration where axons are accompanied by supporting glia (Kim et al., *Exp. Neurol.* 209:313-20 (2008); and Chew et al., *Adv. Funct. Mater.* 17:188-96 (2007)).

Robust growth was observed exclusively from the rostral spinal cord. This response is due to regeneration of host tissue as mechanical effects (e.g., spinal cord/graft movement) cannot explain the outcome for several reasons. Up to 2 mm of spinal cord tissue was surgically removed to guarantee a 3 mm gap (FIG. 4). Other groups that reported caudal migration of the rostral stump (Nomura et al., *Neurosurgery* 58:183-92 (2006)) did not remove tissue, relying on a gap created by a single complete transection. However, this gap may shorten immediately after surgery, leading to potential misinterpretation of results from late time points. To avoid graft migration, the conduits described below were fabricated to include a middle insert (FIG. 1F and FIG. 3H) that presents a mechanical barrier to movement. If rostral graft migration explains the rostrocaudal response, a 3 mm gap would have been present at a more caudal location. Moreover, these mechanical factors would manifest early after injury/implantation. In the examples below, such responses were not observed one week after implantation. Additionally, a number of experimental considerations support this interpretation. First, the robust rostrocaudal response was time-dependent and therefore indicative of regeneration. One week after injury, no differences were observed (FIGS. 8A-8C and FIGS. 10A-10C). By two weeks, a difference in axonal growth in the aligned fiber group was apparent and became significant by 4 weeks (FIGS. 6, 8, and 10). Second, the response was group-specific. At 4 weeks, 7/7 animals in the aligned fiber group had a robust regeneration response 1.5 mm into the conduit, whereas no animals from the film group had this response at the same distance (FIG. 8K). Third, the data from the 4 week time point was collected over two independent experiments and results were consistent between experiments. In a third independent experiment, conduits were re-exposed at 4 weeks in 6 animals that received aligned fiber grafts. The grafts for each of the. 6 animals retained their original placement, and conduits contained a large diameter tissue cable within their lumen, continuous with the rostral and caudal spinal cord stumps. Thus the observed rostrocaudal response is true regeneration of host neural tissue.

An important distinction between this work and that of others is that isolated pioneering axons are followed by bulk regeneration of axons accompanied by astrocytes (FIGS. 10J-10L, 12B, and 12D). Although astrocytes supported bulk regeneration of axons, isolated pioneer axons were found to lead the response, in particular, a number of cells contributed to complete transection gap closure and integrated ahead of the regeneration response with polymer fibers that had detached from the conduit wall (FIGS. 12A and 12C). This response is reminiscent of staggered corticospinal tract development where pioneer axon growth precedes the bulk growth of fasciculating corticospinal axons (Joosten, *Biomaterials* 29:3117-27 (1994); and Schreyer and Jones, Neuroscience 7:1837-53 (1982)).

Aligned fiber conduits promoted significantly greater regeneration than the random fiber control (FIG. 8J). This difference is likely due to the ability of aligned fibers to promote efficient regeneration. In order to examine growth efficiency, the growth of DRG neurites from explants cultured on aligned fibers to those from DRG cultured on film and random fiber substrates (FIG. 2) were compared. Consistent with previous reports (Corey et al., *J. Biomed. Mater. Res. A.* 83:636-45 (2007); Kim et al., *Exp. Neurol.* 209:313-20 (2008): Wang el at., *J. Neural Eng.* 6:016001 (2009); Wang et al., Acta. Biomater. 6:2970-8 (2010); and Xie et al., *ACS Nano.* 3: 1151-9 (2009a)), aligned fibers demonstrated an ability to guide growth of DRG neurites. Importantly, the contact guidance provided by aligned microfibers allowed neurites to reach longer distances (FIGS. 2G and 2H), a desired characteristic for neural tissue repair. Other groups have used aligned micro/nano fiber based conduits to bridge long (>15 mm in rats) peripheral nerve gaps (Chew et al., *Adv. Funct. Mater.* 17:1288-96 (2007); and Kim et al., *Exp. Neurol.* 209:313-20 (2008)). The results described herein for the CNS are in accordance with those of others in the PNS showing that axon regeneration was enhanced in the longitudinally aligned fiber group over random (Kim et al., 2008) or circumferentially oriented fibers (Chew et al., 2007). In the CNS, electrospun fibers have been used to deliver Rolipram after lateral spinal cord hemisection (Zhu et al., *Adv. Fund. Mater.* 20:1-8 (2010)). The data described herein substantiate this indication that electrospun fibers enhance regeneration after spinal cord injury.

Plant et al., *Mol. Cell Neurosci.* 17:471-87 (2001). suggest several potential contributors to rostral/caudal asymmetry, including (1) Wallerian degeneration of descending or ascending axons; (2) supraspinal versus propriospinal and afferent sensory axon capacity for regeneration; (3) incontiguous cerebrospinal fluid flow; (4) amount and character of angiogenesis in the graft and stumps; (5) number/activation state of infiltrating macrophages; and (6) astrocyte reactivity. As discussed in the examples below, a dense matrix at the caudal stump was observed as early as 1 week post injury (FIG. 5C). Although other studies in the PNS show that a similar matrix forms at the rostral edge of the graft (Coumans et al., 2001: Xu et al., 1995b), this effect was not observed in random or aligned fiber conduits (FIGS. 6B and 6C). Another clear difference between spinal cord stumps was the astrocytic dieback observed in the distal stump in all groups. Additionally, differences were observed in the character of angiogenesis between the rostral and caudal stumps (FIG. 1C). Parallel arrays of longitudinally aligned blood vessels encompass the regeneration response at the rostral edge of the conduit, whereas angiogenesis is disorganized at the caudal interface. Also the extent of vascularization seems greater at the caudal graft interface (FIG. 7C), Thus, although long distance axonal regeneration in the CNS was previously thought to occur only in the presence of growth permissive biological substrates, the results described herein demonstrate the ability of adult CNS tissue to regenerate extensively without administration of cells, neurotrophins, antibodies, enzymes, or chemical compounds. Grafts containing aligned micro fibers promote regeneration of CNS tissue composed of regenerating axons from supraspinal and propriospinal neurons accompanied by glial cells. Indeed, this robust response represents a new mode of CNS regeneration.

Accordingly, the present invention is directed to three-dimensional scaffolds including at least one layer of highly-aligned fibers. In addition, the invention relates to use of such scaffolds to treat CNS injury. The invention also includes using such scaffolds in combination with an agent to treat CNS injury.

The results reported herein were obtained using the following methods and materials.

Materials Fabrication

Electrospinning: Thin polymeric films were prepared by casting a PLA solution (4% w/w PLA in a 1:1 dichloromethane:chloroform organic solvent) onto 15×15 mm glass coverslips. Fibers were electrospun onto coverslips mounted on a grounded aluminum target. A 15 kV potential was used to electrospin an 8% w/w PLA solution onto a stationary target to generate random fibers, or a target rotating at 1500 rpm to generate aligned fibers (FIG. 1) (Wang et al., *J. Neural Eng.* 6:27-41 (2009), which is hereby incorporated by reference).

Conduit assembly: PLA films (with or without electrospun fibers) were peeled from coverslips for conduit fabrication. Two specimens of the same type were placed back-to-back and rolled into conduits (FIG. 1). A middle insert was created within the conduit lumen to increase the surface area for cell-substrate interaction (Clements et al., *Biomaterials* 30:3834-46 (2009)) and to decrease the probability of tube collapse (Xu et al., *J. Comp. Neurol.* 351:145-60 (1995b)).

Characterization: Alignment of polymeric fibers was assessed in scanning electron microscopy (SEM) micrographs before and after conduit assembly using previously described methods (Kim et al., *Exp. Neurol.* 209:313-20 (2008); and Wang et al., 2009). Specimens were coated with gold (5 nm) by sputter deposition and micrograph images were taken using a Hitachi S-4700 FES EM. Fiber alignment was quantified by measuring the angle between a given fiber and the median fiber orientation. Angle difference was recorded for fifty fibers from each of 3 independently fabricated specimens (total of 150 fibers per condition) (Wang et al., 2009).

Cell Culture

Dorsal root ganglia: All animal procedures were conducted in accordance with protocols approved by the Institutional Animal Care and Use Committee (IACUC) at The Johns Hopkins University. DRG were isolated from P4 Sprague-Dawley rat pups (Kim et al., 2008). After removing the roots, ganglia were split into halves and cultured on film, random, or aligned fiber specimens for 5 days in neurobasal media with B-27 and nerve growth factor (50 ng/ml).

Astrocytes: Astrocytes were isolated from newborn (P1-2) Sprague-Dawley rats (Smith and Strunz, *Glia* 52:209-18 (2005)). Cerebral cortices were isolated, meninges removed, and tissue was treated with 0.01% trypsin and mechanically dissociated by trituration through a Pasteur pipette. Cells were then plated on poly-D-lysine (10 μg/ml) coated flasks, and maintained in culture for 10 days. Cultures were purified for astrocytes by vigorous shaking to remove non-adherent cells. Astrocytes were plated onto film, random, or aligned fiber specimens at a density of 4000 cells $cm^{-2}$ and maintained for 48 hrs in culture.

Immunocytochemistry: Cells were fixed 1 hour in 4% PFA and blocked for 1 hour in PBS/10% normal goat serum (Sigma-Aldrich) and 0.4% triton-X (Sigma-Aldrich). DRG were incubated overnight at 4° C. with chicken anti-neurofilament (NF, 1:1000: Millipore, Temecula, CA), and astrocyte cultures with rabbit anti-GFAP (1:1000: Dako, Carpinteria, CA) primary antibodies. Specimens were subsequently incubated for 1 hour with goat anti-chicken Alexa-488 or goat anti-rabbit Alexa-680 conjugated secondary antibodies. Ceils were counterstained with Hoechst (H, 1:2000) and mounted on glass slides for imaging using either an Olympus BX61 upright fluorescence microscope or an Olympus Fluoview FV1000 confocal microscope.

Quantitative analysis: Neurite extension was analyzed by separately fitting DRG explants (n=6) and fields of neurite extension from fluorescent neurofilament images to an elliptical model using least-squares regression (Xie et al., *ACS Nano.* 3:1151-9 (2009a); and Xie et al., *Biomaterials* 30:354 62 (2009b)). From these images, eccentricity and maximum/average neurite distance were calculated. Eccentricity was used as a measure of anisotropy where 0 (in the case of a perfect circle) represents no preferential direction of neurite extension and 1 (in the case of straight line) represents perfect directionality.

Complete Transection Model of Spinal Cord Injury

Animals: Female Sprague-Dawley rats (N=45, 250 g; Harlan, Indianapolis, Ind.) were housed according to NIH and USD A guidelines. The IACUC of Johns Hopkins University approved all animal procedures. Rats were randomly divided into 3 groups (film, n=13; random, n=13; aligned fiber, n=19) and were euthanized at 1 (n=9, 3 per group), 2 (n=9, 3 per group), and 4 (n=27, 7 film, 7 random and 13 aligned) weeks after conduit implantation. Importantly, the data for the 4 week time point was acquired in two separate experiments. A third group of animals (n=6) from the aligned fibers conduits was used for retrograde tracing.

Figure 4A:
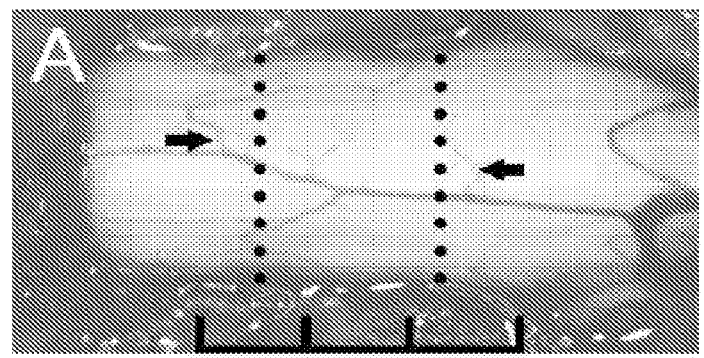
FIGS. 4A-4F include images showing complete transection spinal cord injury. A laminectomy was performed at thoracic level 8, exposing the thoracic 9/10 spinal cord. A first cut was made toward the rostral end of the laminectomy (FIG. 4A), the cord was allowed to retract, and a second cut was made 3 mm from the rostral stump (FIG. 4B). Arrows indicate anatomical landmarks before and after transection. A 3 mm gap in the spinal cord was made by removing 1-2 mm of spinal cord tissue (FIGS. 4B and 4C), and a 3 mm long conduit was grafted between the rostral and caudal stumps (FIGS. 4D).
Figure 4B:
Figure 4C:
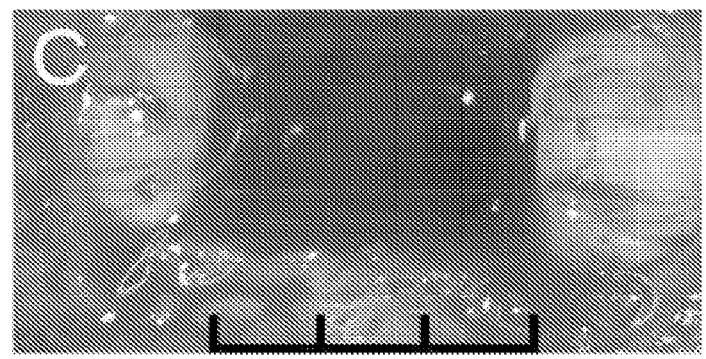
Figure 4D:
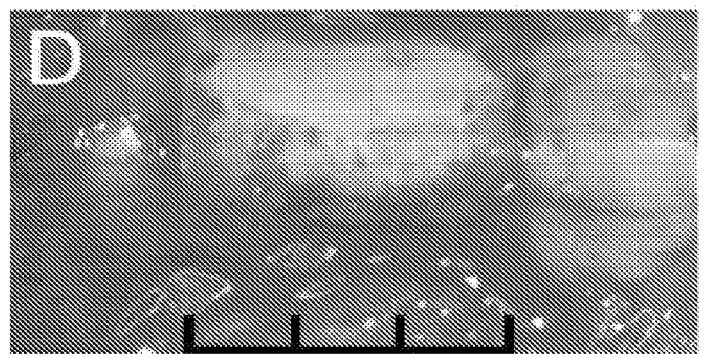

Conduit implantation Rats were anesthetized with an IM injection of 60 mg/kg ketamine and 0.4 mg/kg metidomidine. Animal backs were shaved and aseptically prepared, and ophthalmic ointment (Lacrilube; Allergen Pharmaceuticals, Irvine, Calif.) was applied. Spinal cord complete transection and conduit implantation were performed as described previously (Hurtado et al., *Biomaterials* 27:430-42 (2006)). After opening the skin and muscle layers, a restricted dorsal laminectomy (FIG. 4A) was performed on the thoracic eight (T8) vertebra and the dura mater was carefully opened. The exposed T9-10 spinal cord was transected using angled scissors; a first cut was made at the rostral end of the laminectomy (FIG. 4B) and then 1-2 mm of tissue were completely removed creating a 3 mm gap (FIG. 4C). After hemostasis was achieved, a 3 mm long conduit (film, random, or aligned fiber) was implanted to bridge the gap between the rostral and caudal spinal cord stumps (FIG. 4D). Prior to implantation, all conduits were filled with a solution of 1% fibrinogen (Type 1, human plasma; Sigma-Aldrich) in DMEM with 2% $CaCl_2$, 2% aprotinin (Sigma-Aldrich), and 0.2% gentamicin (Gibco). After conduit implantation, hoer of silicone sheeting (0.005" thick) was placed over the implant and both cord stumps. Muscle layers were sutured and the skin was closed with metal wound clips. During surgery, rats were kept on a heating pad to maintain body temperature, immediately after surgery, rats received 10 ml of warm (37° C.) Ringers' solution subcutaneously and 0.03 ml of gentamicin (40 mg/ml; Buck, Inc.,. Owings Mills, Mo.) intramuscularly. Anesthesia was reversed with an IM injection of 0.05 ml (1 mg/kg) atipamezole hydrochloride (Antisedan®; Pfizer Animal Health, Exton, Pa.). All animals were allowed to recover from anesthesia in a small animal incubator set at 30° C. After fail recovery, rats were returned to their cages with ad libitum water and food. Gentamicin (0.03 ml) was administered IM daily for seven days to prevent urinary tract infection. Bladders were expressed manually twice a day until reflex bladder voiding returned. Throughout further survival, bladders as well as general health of the rats were monitored at least once a day. In cases of urinary tract infection, gentamicin administration was reinitiated for 7-10 days.

Assessment of hindlimb motor function: In rats that survived for 4 weeks, changes in hindlimb function were assessed using the test developed by Basso, Beattie, and Bresnahan (Basso et al., *J. Neurotrauma* 12:1-21 (1995); and Basso et al., *Exp. Neurol.* 139:214-56 (1996)), an open field test with a 22-point scale (0 represents no movement of hindlimbs and 21 represents normal locomotion). During the week before surgery, rats were tested twice to become accustomed to the testing environment. During, survival after surgery, rats were tested once a week for minutes by two independent observers without knowledge of the experimental paradigms.

Retrograde axonal tracing: Fast blue tracer was injected in the middle of the conduit of 6 additional animals from the aligned fiber group. Four weeks after injury and conduit implantation rats were anesthetized and prepared for surgery as above. Scar tissue was gently removed and the implanted conduit was re-exposed. A midline longitudinal incision through the dorsal surface of the conduit was made using angled microscissors (Fine Science Tools, Foster City, CA, USA) exposing the regenerated tissue and using a glass needle attached to a 1 µl Hamilton syringe, 0.5 µl of Fast blue injected 1.5 mm caudal to the rostral end of the conduit at a rate of 0.25 µl/min. The needle was left in place for an additional 2 minutes to avoid tracer leakage and then slowly withdrawn (Hurtado et al., 2006). Muscle layers were sutured, the skin was closed with metal wound clips, and animals received postoperative care as above. Rats were perfused (see below) 7 days later.

Figure 4E:
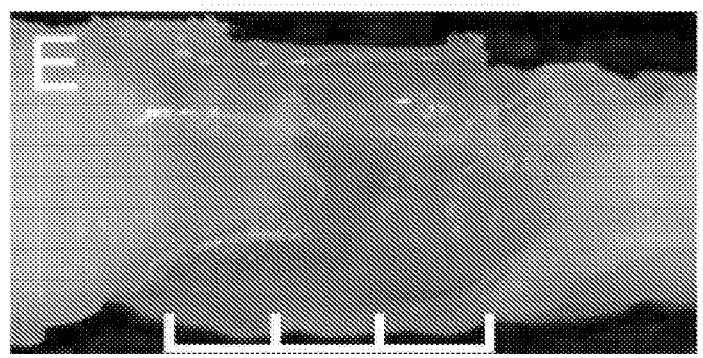
Figure 4F:
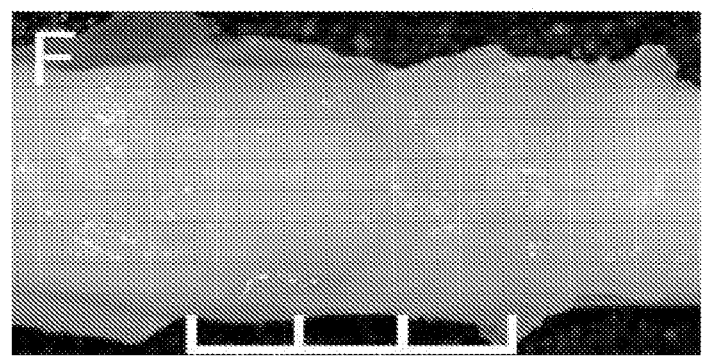

Tissue preparation and immunohistochemistry: One, two, and four weeks after conduit implantation, rats were anaesthetized as above. After deep anaesthesia was confirmed, the heart was exposed and 500 IU of Heparin (Henry Schein, Melville, NY, USA) was injected into the left ventricle. Next. 300 ml of 1×PBS followed by 300 ml ice-cold 4% PFA in 1×PBS was perfused through the vascular system. Spinal cords were removed and post fixed overnight at C in the same fixative. A 15 mm long segment centered on the conduit and including the rostral and caudal spinal cord stumps as well as a 10 min segment inducting the brainstem were dissected and transferred to phosphate-buffered 30% sucrose (FIGS. 4E and 4F show conduits 1 and 4 weeks after implantation, respectively). After 48 hours, tissue was frozen within shandon M-1 embedding matrix (Thermo Electron Corporation, Pittsburgh, PA, USA). From these spinal cords, 20 µm thick horizontal sections were cut on a cryostat, mounted onto glass slides, and stored at −20° C. Brains and brainstems were cut into 40 µm thick coronal sections, mounted onto glass slides and stored at −20° C. Spinal cord cryostat sections were permeabilized with 0.3% Triton X-100 in PB (0.1 M, pH 7.4), immuno-blocked with 5% normal goat serum in PB at room temperature for 30 min, and then immunostained as described before (Hurtado et al., 2006). The following primary antibodies were used: rabbit antibodies against glial fibrillary acidic protein (GFAP, 1:200; Incstar Corp., Stillwater, MN.), serotonin (5HT, 1:200; Immunostar, Hudson, Wis.) and laminin (LAM, 1:400; Sigma-Aldrich). Mouse antibodies were directed against neurofilament (RT97, 1:5; Developmental Studies Hybridoma Bank), and rat endothelial cell antigen (RECA-1, 1:25; Serotec), Stained sections were coverslipped using Vectashield/DAPI (Vector Laboratories, Inc. Burlingame, CA) and kept at 4° C. until analysis. Adjacent sections were stained using cresyl violet. Images were taken on either an inverted Olympus IX70 microscope or an Olympus Fluoview 1000 confocal system at an original magnification of 20× with individual filter sets for each channel, and were assembled using Adobe Photoshop CS3.

Quantitative analysis: Tissue volume was assessed in the cresyl violet stained sections using the Cavalieri estimator probe (grid spacing: 250 µm) from StereoInvestigator® (MBF Bioscience, Williston, VT). From each animal, every tenth cryostat section (200 µm intervals) was used to determine the volume of tissue inside the conduit; tissue volume is expressed as the percentage of conduit lumen containing Nissl stained cell bodies. The distance between the rostral edge of the conduit to the 'axonal front', defined as the point at which there is a group of 10 or more contiguous fibers, was quantified at all tune points in the RT97/GFAP-stained sections (Shen et al., 2009). The number of animals that had grown CNS tissue (defined by presence of RT97 and GFAP inside the conduit) was quantified for animals surviving 4 weeks at the rostral graft interface and every 2.50 µm in the rostrocaudal direction. Fast Blue labeled neurons were counted on every sixth 40 µm-thick coronal section throughout the brainstem. Sections were scanned at 20× and all cells were counted after morphological confirmation under 40× magnification.

Statistical Analysis

JMP IN software (Release 7.0.2; SAS, Cary, NC) was used to carry out all statistical analyses. A one-way ANOVA test was performed to determine statistical differences between groups for eccentricity, maximum neurite length, average neurite length, and, percentage of conduit filled with tissue, if groups were statistically different in the ANOVA test, a post-hoc Tukey-Kramer HSD test was used to compare ad pairs individually. Repeated measures ANOVA was used to determine whether differences between groups mean hindlimb BBB scores were statistically significant, P≤0.05 was considered to be statistically significant. All data are presented as mean±SEM.

Other Embodiments

From the foregoing description, it will be apparent that variations and modifications may be made to the invention described herein to adopt it to various usages and conditions. Such embodiments are also within the scope of the following claims.

We claim:

1. A method for fabricating a three-dimensional scaffold, the method comprising:
   electrospinning a plurality of fibers to produce at least one layer of highly-aligned fibers; and
   forming the at least one layer of highly-aligned fibers into a three-dimensional scaffold without disturbing the alignment of the highly-aligned polymer fibers,
   wherein the at least one layer of highly-aligned fibers is curved in a direction substantially perpendicular to a general direction of the fibers,
   wherein the at least one layer of highly-aligned fibers includes an outer profile and an inner profile, and
   wherein the at least one layer of highly-aligned fibers is configured to be implanted into the body such that the outer profile is substantially circular, and wherein the inner profile is, when viewed in the general direction of the fibers, selected from the group consisting of: an S-shaped profile, an I-shaped profile, a W-shaped profile, a Z-shaped profile, and a helicoid.

2. The method of claim 1, wherein the plurality of highly-aligned fibers are electrospun onto a base layer.

3. The method of claim 2, wherein the base layer includes a polymer film.

4. The method of claim 3, wherein the polymer film is porous.

5. The method of claim 2, wherein the base layer has a sufficient thickness to inhibit growth of neural axons through the base layer.

6. The method of claim 2, wherein the fibers are biocompatible.

7. The method of claim 2, further comprising:
bonding one or more edges of the three-dimensional scaffold to maintain a shape of the three-dimensional scaffold.

8. The method of claim 1, wherein the fibers are fabricated from one or more polymers selected from the group consisting of: poly-L-lactic acid (PLLA), polylactic-co-glycolic acid (MCA), PLGA coated with polypyrrole, polycaprolactone, poly(ethersulfone), poly(acrylonitrile-co-methylacrylate) (PAN-MA), and combinations thereof.

9. The method of claim 1, further comprising:
applying a chemoattractant to the highly-aligned fibers.

10. The method of claim 1, wherein the at least one layer of highly-aligned fibers is curved to form an S-shaped profile when viewed in a general direction of the fibers.

11. The method of claim 1, wherein the at least one layer of highly-aligned fibers is curved to substantially define a conduit, and wherein the conduit has an external diameter between about 2.0 mm and about 2.5 mm.

12. The method of claim 1, wherein the highly.-aligned fibers have a mean diameter between about 1.0 micron and about 1.2 microns.

13. The method of claim 1, wherein the three-dimensional scaffold further comprises a therapeutic agent.

14. The method of claim 1, wherein the three-dimensional scaffold further comprises a cellular substrate.

* * * * *

UNITED STATES PATENT AND TRADEMARK OFFICE
CERTIFICATE OF CORRECTION

PATENT NO. : 11,980,534 B2
APPLICATION NO. : 16/524473
DATED : May 14, 2024
INVENTOR(S) : Andres Hurtado et al.

Page 1 of 1

It is certified that error appears in the above-identified patent and that said Letters Patent is hereby corrected as shown below:

On the Title Page

Item (73) Assignees: The second Assignee, Johns Hopkins University, Baltimore, MD (US), should be The Johns Hopkins University, Baltimore, MD (US)

Signed and Sealed this
Tenth Day of September, 2024

Katherine Kelly Vidal
*Director of the United States Patent and Trademark Office*